(12) United States Patent
Hartley et al.

(10) Patent No.: US 7,970,470 B2
(45) Date of Patent: Jun. 28, 2011

(54) DIAGNOSIS AND/OR THERAPY USING BLOOD CHEMISTRY/EXPIRED GAS PARAMETER ANALYSIS

(75) Inventors: Jesse W. Hartley, Lino Lakes, MN (US); Jeffrey E. Stahmann, Ramsey, MN (US); Kent Lee, Fridley, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1275 days.

(21) Appl. No.: 10/929,830

(22) Filed: Aug. 30, 2004

(65) Prior Publication Data

US 2005/0065572 A1 Mar. 24, 2005

Related U.S. Application Data

(60) Provisional application No. 60/504,308, filed on Sep. 18, 2003.

(51) Int. Cl.
*A61N 1/00* (2006.01)
*A61B 5/00* (2006.01)
*A61B 5/05* (2006.01)

(52) U.S. Cl. ............... 607/22; 607/20; 607/21; 607/42; 600/309; 600/310; 600/345

(58) Field of Classification Search .............. 607/20–22, 607/42; 600/309–310, 345
See application file for complete search history.

(56) References Cited

U.S. PATENT DOCUMENTS

| | | | |
|---|---|---|---|
| 4,312,734 A | 1/1982 | Nichols | |
| 4,390,405 A | 6/1983 | Hahn et al. | |
| 4,562,841 A | 1/1986 | Brockway et al. | |
| 4,721,110 A * | 1/1988 | Lampadius | 607/20 |
| 4,807,629 A * | 2/1989 | Baudino et al. | 607/22 |
| 4,827,935 A | 5/1989 | Geddes et al. | |
| 4,886,064 A * | 12/1989 | Strandberg | 607/18 |
| 5,036,849 A | 8/1991 | Hauck et al. | |
| 5,178,156 A | 1/1993 | Takishima et al. | |
| 5,203,348 A | 4/1993 | Dahl et al. | |
| 5,230,337 A | 7/1993 | Dahl et al. | |
| 5,243,979 A * | 9/1993 | Stein et al. | 607/20 |
| 5,284,136 A | 2/1994 | Hauck et al. | |

(Continued)

FOREIGN PATENT DOCUMENTS

EP 317986 A1 * 5/1989

(Continued)

OTHER PUBLICATIONS

Reddel et al., *Analysis of Adherence to Peak Flow Monitoring When Recording of Data is Electronic*, BMJ 146-147 (2002).

(Continued)

*Primary Examiner* — Niketa I Patel
*Assistant Examiner* — Nicole F Lavert
(74) *Attorney, Agent, or Firm* — Hollingsworth & Funk, LLC

(57) ABSTRACT

Methods and systems for diagnosing disorders, including, for example, disordered breathing, involve sensing one or more of a blood chemistry parameter and/or an expired gas parameter, such as expired respiratory gas concentration, blood gas concentration, and blood pH. Diagnosis of the disorder may be performed by a medical device, such as a respiratory therapy device or a cardiac therapy device, based on implantably detected blood gas/pH concentration/level or externally detected expired respiratory gas concentration. Cardiac and respiratory therapies for addressing the disorder may be adjusted based on the detected parameters.

30 Claims, 14 Drawing Sheets

U.S. PATENT DOCUMENTS

| | | | |
|---|---|---|---|
| 5,313,953 A | 5/1994 | Yomtov et al. | |
| 5,360,442 A | 11/1994 | Dahl et al. | |
| 5,366,496 A | 11/1994 | Dahl et al. | |
| 5,376,476 A | 12/1994 | Eylon | |
| 5,388,578 A | 2/1995 | Yomtov et al. | |
| 5,391,200 A | 2/1995 | KenKnight et al. | |
| 5,397,342 A | 3/1995 | Heil, Jr. et al. | |
| 5,398,682 A | 3/1995 | Lynn | |
| 5,404,877 A * | 4/1995 | Nolan et al. | 600/484 |
| 5,411,031 A | 5/1995 | Yomtov | |
| 5,540,727 A | 7/1996 | Tockman et al. | |
| 5,545,202 A | 8/1996 | Dahl et al. | |
| 5,593,431 A | 1/1997 | Sheldon | |
| 5,603,732 A | 2/1997 | Dahl et al. | |
| 5,605,151 A | 2/1997 | Lynn | |
| 5,632,281 A | 5/1997 | Rayburn | |
| 5,704,345 A | 1/1998 | Berthon-Jones | |
| 5,794,615 A * | 8/1998 | Estes | 128/204.23 |
| 5,836,987 A | 11/1998 | Baumann et al. | |
| 5,916,243 A | 6/1999 | KenKnight et al. | |
| 5,974,340 A * | 10/1999 | Kadhiresan | 607/18 |
| 5,974,349 A | 10/1999 | Levine | |
| 6,041,777 A * | 3/2000 | Faithfull et al. | 128/200.24 |
| 6,044,297 A | 3/2000 | Sheldon et al. | |
| 6,044,298 A | 3/2000 | Salo et al. | |
| 6,055,454 A | 4/2000 | Heemels | |
| 6,064,910 A * | 5/2000 | Andersson et al. | 607/20 |
| 6,141,590 A * | 10/2000 | Renirie et al. | 607/20 |
| 6,144,866 A | 11/2000 | Miesel et al. | |
| 6,148,814 A | 11/2000 | Clemmer et al. | |
| 6,221,011 B1 | 4/2001 | Bardy | |
| 6,236,873 B1 | 5/2001 | Holmström | |
| 6,264,606 B1 * | 7/2001 | Ekwall et al. | 600/300 |
| 6,270,457 B1 | 8/2001 | Bardy | |
| 6,275,727 B1 * | 8/2001 | Hopper et al. | 600/513 |
| 6,277,072 B1 | 8/2001 | Bardy | |
| 6,280,380 B1 | 8/2001 | Bardy | |
| 6,312,378 B1 | 11/2001 | Bardy | |
| 6,336,903 B1 | 1/2002 | Bardy | |
| 6,358,203 B2 | 3/2002 | Bardy | |
| 6,368,284 B1 | 4/2002 | Bardy | |
| 6,398,728 B1 | 6/2002 | Bardy | |
| 6,409,675 B1 | 6/2002 | Turcott | |
| 6,411,850 B1 * | 6/2002 | Kay et al. | 607/20 |
| 6,440,066 B1 | 8/2002 | Bardy | |
| 6,459,929 B1 * | 10/2002 | Hopper et al. | 600/513 |
| 6,467,333 B2 | 10/2002 | Lewis et al. | |
| 6,527,729 B1 | 3/2003 | Turcott | |
| 6,574,507 B1 * | 6/2003 | Bonnet | 607/20 |
| 6,595,928 B2 | 7/2003 | Mansy et al. | |
| 6,600,949 B1 | 7/2003 | Turcott | |
| 6,641,542 B2 * | 11/2003 | Cho et al. | 600/529 |
| 6,658,292 B2 | 12/2003 | Kroll et al. | |
| 6,662,032 B1 | 12/2003 | Gavish et al. | |
| 6,731,984 B2 * | 5/2004 | Cho et al. | 607/17 |
| 6,741,885 B1 * | 5/2004 | Park et al. | 600/509 |
| 6,748,252 B2 | 6/2004 | Lynn et al. | |
| 6,752,765 B1 * | 6/2004 | Jensen et al. | 600/536 |
| 6,830,548 B2 * | 12/2004 | Bonnet et al. | 600/529 |
| 6,910,481 B2 | 6/2005 | Kimmel et al. | |
| 6,928,324 B2 * | 8/2005 | Park et al. | 607/20 |
| 7,025,730 B2 * | 4/2006 | Cho et al. | 600/529 |
| 7,092,755 B2 | 8/2006 | Florio | |
| 7,130,687 B2 * | 10/2006 | Cho et al. | 607/17 |
| 7,136,704 B2 * | 11/2006 | Schulman | 607/22 |
| 7,184,817 B2 * | 2/2007 | Zhu et al. | 600/513 |
| 7,225,021 B1 * | 5/2007 | Park et al. | 607/18 |
| 7,231,250 B2 * | 6/2007 | Band et al. | 607/18 |
| 7,252,640 B2 * | 8/2007 | Ni et al. | 600/538 |
| 7,269,459 B1 * | 9/2007 | Koh | 607/20 |
| 7,302,295 B2 * | 11/2007 | Stahmann et al. | 607/20 |
| 2002/0173728 A1 * | 11/2002 | Mault | 600/531 |
| 2002/0193697 A1 * | 12/2002 | Cho et al. | 600/529 |
| 2003/0023184 A1 | 1/2003 | Pitts-Crick et al. | |
| 2003/0073919 A1 | 4/2003 | Hampton et al. | |
| 2003/0083241 A1 * | 5/2003 | Young | 514/9 |
| 2003/0100925 A1 | 5/2003 | Pape et al. | |
| 2003/0121519 A1 * | 7/2003 | Estes et al. | 128/204.18 |
| 2003/0139780 A1 * | 7/2003 | Markowitz et al. | 607/17 |
| 2003/0171687 A1 | 9/2003 | Irie et al. | |
| 2003/0181820 A1 * | 9/2003 | Orr et al. | 600/529 |
| 2003/0209246 A1 * | 11/2003 | Schroeder et al. | 128/204.17 |
| 2004/0039605 A1 | 2/2004 | Bardy | |
| 2004/0059240 A1 | 3/2004 | Cho et al. | |
| 2004/0088027 A1 | 5/2004 | Burnes et al. | |
| 2004/0111040 A1 * | 6/2004 | Ni et al. | 600/534 |
| 2004/0133079 A1 | 7/2004 | Mazar et al. | |
| 2004/0138719 A1 | 7/2004 | Cho et al. | |
| 2004/0186523 A1 | 9/2004 | Florio | |
| 2004/0210154 A1 | 10/2004 | Kline | |
| 2005/0039745 A1 * | 2/2005 | Stahmann et al. | 128/204.18 |
| 2005/0042589 A1 * | 2/2005 | Hatlestad et al. | 434/262 |
| 2005/0043644 A1 * | 2/2005 | Stahmann et al. | 600/529 |
| 2005/0065572 A1 * | 3/2005 | Hartley et al. | 607/42 |
| 2005/0142070 A1 | 6/2005 | Hartley et al. | |
| 2005/0159784 A1 * | 7/2005 | Arceta | 607/20 |
| 2005/0240240 A1 * | 10/2005 | Park et al. | 607/42 |
| 2006/0293714 A1 * | 12/2006 | Salo et al. | 607/9 |
| 2007/0005114 A1 * | 1/2007 | Salo et al. | 607/17 |
| 2007/0112388 A1 * | 5/2007 | Salo | 607/21 |
| 2007/0150014 A1 * | 6/2007 | Kramer et al. | 607/17 |

FOREIGN PATENT DOCUMENTS

| | | |
|---|---|---|
| EP | 1151718 | 11/2001 |
| WO | 99/04841 | 2/1999 |
| WO | WO 9904841 A1 * | 2/1999 |
| WO | WO0001438 | 1/2000 |
| WO | 02/087696 | 7/2002 |
| WO | WO03075744 | 9/2003 |
| WO | WO 9904841 * | 2/2004 |
| WO | WO2004062485 | 7/2004 |
| WO | WO2005028029 | 3/2005 |

OTHER PUBLICATIONS

Altshule et al., The Effect of Position on Periodic Breathing in Chronic Cardiac Decomposition, New Eng. Journal of Med., vol. 259, No. 22, pp. 1064-1066, Nov. 27, 1958.

Bradley et al., *Sleep Apnea and Heart Failure, Park I: Obstructive Sleep Apnea*, 107 Circulation 1671-1678, 2003.

Dark et al., Breathing Pattern Abnormalities and Arterial Oxygen Desaturation During Sleep in the Congestive Heart Failure Syndrome, Chest, Jun. 1987, 6:833-6.

Hoffman et al., Cheyne-Stokes Respiration in Patients Recovering from Acute Cardiogenic Pulmonary Edema, Chest 1990, 97:410-12.

Junyu et al., Posture Detection Algorithm Using Multi Axis DC-Accelerometer, Pace vol. 22, Apr. 1999.

Rees et al., Paroxysmal Nocturnal Dyspnoea and Periodic Respiration, The Lancet, Dec. 22-29, 1979, pp. 1315-1317.

Tkacova et al., Left Ventricular Volume in Patients with Heart Failure and Cheyne-Strokes Respiration during Sleep, Am. Journal, Respir. Crit. Care Med., vol. 156, pp. 1549-1555, 1997.

* cited by examiner

DIAGNOSIS AND/OR THERAPY USING BLOOD CHEMISTRY/EXPIRED GAS PARAMETER ANALYSIS

RELATED PATENT DOCUMENTS

This application claims the benefit of Provisional Patent Application Ser. No. 60/504,308 filed on Sep. 18, 2003, now expired, "Diagnosis and/or Therapy Using Gas Analysis," to which priority is claimed pursuant to 35 U.S. §119(e) and which is hereby incorporated by reference.

FIELD OF THE INVENTION

The invention relates generally to medical gas therapy systems and methods, and more particularly to systems and methods for diagnosis and/or therapy using measurement of expired gases and/or blood gases.

BACKGROUND OF THE INVENTION

The human body functions through a number of interdependent physiological systems controlled through various mechanical, electrical, and chemical processes. The metabolic state of the body is constantly changing. For example, as exercise level increases, the body consumes more oxygen and gives off more carbon dioxide. The cardiac and pulmonary systems maintain appropriate blood gas levels by making adjustments that bring more oxygen into the system and dispel more carbon dioxide. The cardiovascular system transports blood gases to and from the body tissues. The respiration system, through the breathing mechanism, performs the function of exchanging these gases with the external environment. Together, the cardiac and respiration systems form a larger anatomical and functional unit denoted the cardiopulmonary system.

Various disorders may affect the cardiovascular, respiratory, and other physiological systems. For example, heart failure (HF) is a clinical syndrome that impacts a number of physiological processes. Heart failure is an abnormality of cardiac function that causes cardiac output to fall below a level adequate to meet the metabolic demand of peripheral tissues. Heart failure is usually referred to as congestive heart failure (CHF) due to the accompanying venous and pulmonary congestion. Congestive heart failure may have a variety of underlying causes, including ischemic heart disease (coronary artery disease), hypertension (high blood pressure), and diabetes, among others.

There are a number of diseases and disorders that primarily affect respiration, but also impact other physiological systems. Emphysema and chronic bronchitis are grouped together and are known as chronic obstructive pulmonary disease (COPD). Pulmonary system disease also includes tuberculosis, sarcoidosis, lung cancer, occupation-related lung disease, bacterial and viral infections, and other diseases or disorders. Pulmonary diseases may also affect the acid-base balance of the blood.

Periodic breathing is characterized by cyclic respiratory patterns that may exhibit rhythmic rises and falls in tidal volume. Obstructive periodic breathing is characterized by cyclic respiratory patterns with an obstructive apnea or hypopnea event in each cycle. Periodic breathing may be classified as obstructive, central or mixed. Central periodic breathing involves cyclic respiratory patterns including a central apnea or hypopnea event in each cycle. Periodic breathing may also be of mixed origin. Mixed origin periodic breathing is characterized by cyclic respiratory patterns having a mixture of obstructive and central apnea events in each cycle.

Apnea is a fairly common disorder characterized by periods of interrupted breathing. Apnea is typically classified based on its etiology. One type of apnea, denoted obstructive apnea, occurs when the patient's airway is obstructed by the collapse of soft tissue in the rear of the throat. Central apnea is caused by a derangement of the central nervous system control of respiration. The patient ceases to breathe when control signals from the brain to the respiratory muscles are absent or interrupted. Mixed apnea is a combination of the central and obstructive apnea types. Regardless of the type of apnea, people experiencing an apnea event stop breathing for a period of time. The cessation of breathing may occur repeatedly during sleep, sometimes hundreds of times a night and sometimes for a minute or longer.

In addition to apnea, other types of disordered respiration cycles have been identified, including hypopnea (shallow breathing), tachypnea (rapid breathing), hyperpnea (heavy breathing), and dyspnea (labored breathing). Combinations of the respiratory cycles described above may be observed, including, for example, periodic breathing and Cheyne-Stokes respiration (CSR). Cheyne-Stokes respiration is a specific form of periodic breathing wherein the tidal volume decreases to zero resulting in apneic intervals. The breathing interruptions of periodic breathing and CSR may be associated with central apnea, or may be obstructive in nature. CSR is frequently observed in patients with congestive heart failure (CHF) and is associated with an increased risk of accelerated CHF progression. Because of the cardiopulmonary implications, detection and therapy for disordered breathing is of particular interest.

Chronic obstructive pulmonary disease generally develops over many years, typically from exposure to cigarette smoke, pollution, or other irritants. Over time, the elasticity of the lung tissue is lost, and the lungs become distended, unable to expand and contract normally. As the disease progresses, breathing becomes labored, and the patient grows progressively weaker.

Disordered breathing is a respiratory system disorder that affects a significant percentage of patients between 30 and 60 years. Disordered breathing, including apnea and hypopnea, may be caused, for example, by an obstructed airway, or by derangement of the signals from the brain controlling respiration. Sleep disordered breathing is particularly prevalent and is associated with excessive daytime sleepiness, systemic hypertension, increased risk of stroke, angina and myocardial infarction. Disordered breathing can be particularly serious for patients concurrently suffering from cardiovascular deficiencies.

There are a number of cardiovascular system disorders that have secondary effects with respect to other physiological systems. When functioning properly, the human heart maintains its own intrinsic rhythm, and is capable of pumping an adequate amount of blood throughout the body's circulatory system. However, some people have abnormal cardiac rhythms, referred to as cardiac arrhythmias, that cause a decrease in cardiac output.

Bradycardia is a disorder that involves a heartbeat that is abnormally slow, causing insufficient blood supply to the body's tissues. Tachyarrhythmia occurs when the patient's cardiac rhythm is too fast. The excessively rapid cardiac contractions result in diminished blood circulation because the heart has insufficient time to fill with blood before contracting to expel the blood. Ventricular fibrillation is a particularly dangerous form of tachyarrhythmia, and may result in death within minutes if the heart's normal rhythm is not restored.

SUMMARY OF THE INVENTION

Embodiments of the invention are directed to systems and methods for detecting and/or diagnosing disorders, such as disordered breathing, a pulmonary disorder, and/or a cardiac disorder, and providing therapy based on one or more conditions or parameters influenced by such diseases/disorders, such as blood gas concentrations, expired gas concentrations, or blood acid-base balance (i.e., hydrogen ion concentration). In accordance with one embodiment, a method of providing disordered breathing therapy involves determining one or more parameters influence by disordered breathing, which may include one or more of blood gas concentration, expired respiratory gas concentration, or blood hydrogen ion concentration, also known as pH. Respiratory and cardiac therapies may be adjusted based on the one or more detected parameters.

In accordance with another embodiment of the invention, a disordered breathing therapy method involves sensing at least one of an expired respiratory gas concentration, a blood gas concentration, or blood pH. Respiratory and cardiac therapies may be adjusted based on one or more of these parameters.

In a further embodiment of the invention, a medical system includes a detector configured to detect blood gas concentration, expire respiratory gas concentration, or hydrogen ion concentration. The medical system further includes a therapy delivery system. The therapy delivery system includes a respiratory therapy delivery device configured to deliver respiratory therapy to a patient and a cardiac therapy delivery device configured to deliver cardiac therapy to the patient. A therapy controller is coupled to the respiratory therapy delivery device and the cardiac therapy delivery device and is configured to adjust respiratory and cardiac therapies based on the detected blood gas concentration, expired gas concentration, and/or blood pH.

The above summary of the invention is not intended to describe each embodiment or every implementation of the invention. Advantages and attainments, together with a more complete understanding of the invention, will become apparent and appreciated by referring to the following detailed description and claims taken in conjunction with the accompanying drawings.

Figure 1A:
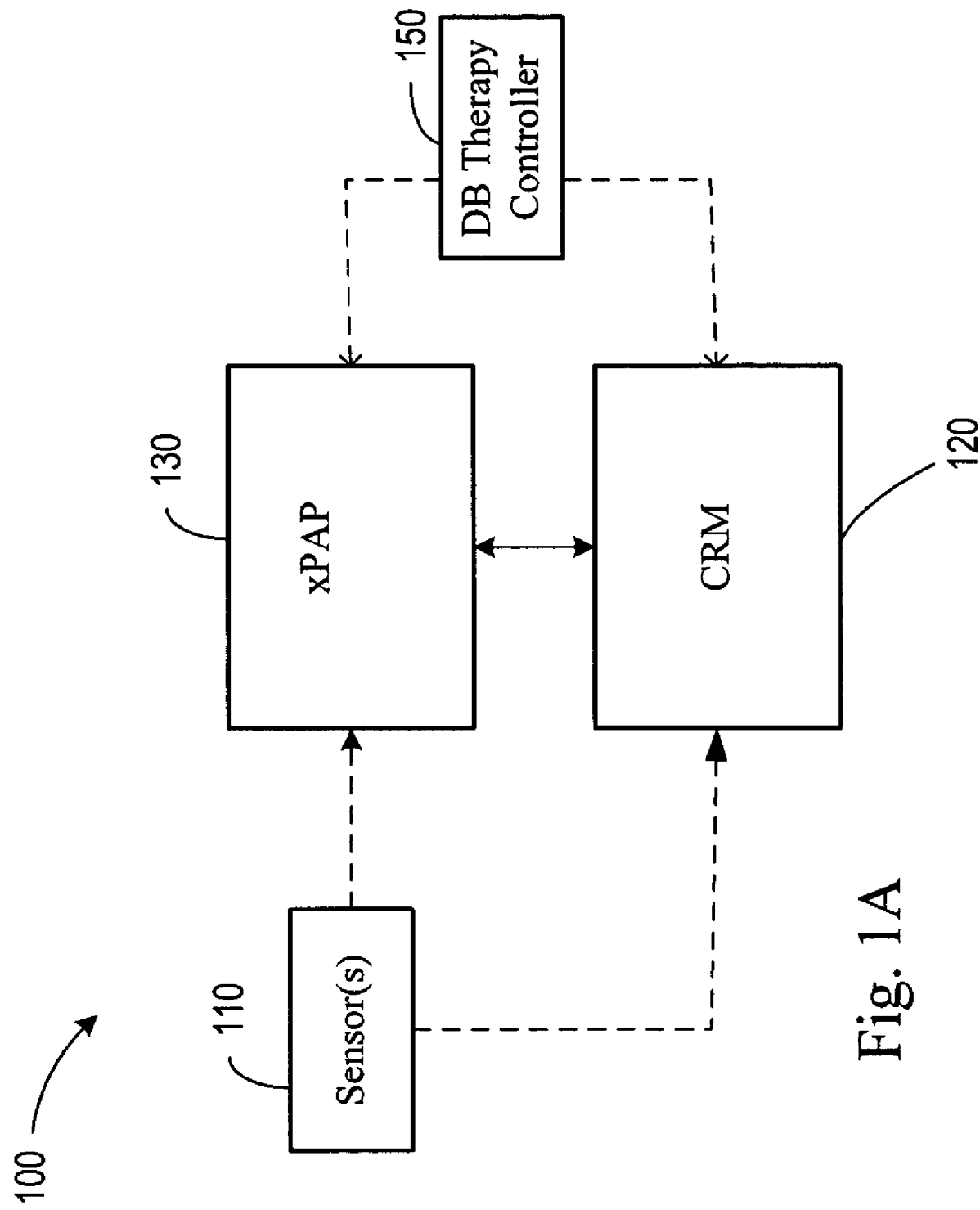
FIG. 1A is a block diagram of a system used to provide measurement of one or more parameters influenced by disordered breathing for diagnosis and therapy in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which are shown by way of illustration, various embodiments by which the invention may be practiced. It is to be understood that other embodiments may be utilized, and structural and functional changes may be made without departing from the scope of the invention.

Methods, devices, and systems in accordance with the invention may include one or more of the features, structures, methods, or combinations thereof described herein. It is intended that methods, devices, and systems in accordance with the invention need not include all of the features and functions described herein, but may be implemented to include selected features and functions that provide for useful structures and/or functionality.

Disorders and diseases affecting the interdependent physiological systems of the human body may be more effectively diagnosed and treated using a coordinated approach. Various embodiments of the invention are implemented using medical systems employing one or a number of patient-external and/or patient-internal medical devices. Medical devices may communicate or otherwise operate in concert or in a stand-alone manner to provide more comprehensive patient monitoring, diagnosis, and therapy.

Many patients suffering from obstructive sleep apnea (OSA) have intermittent oxygen desaturation associated with periods of apnea or hypopnea. Oxygen saturation levels below 90% are considered harmful. Usually, treatment is directed at correcting the apnea, which may in turn prevent hypoxemia. Unfortunately, many patients fail or are not candidates for nasal continuous positive airway pressure (CPAP) or surgical correction of their OSA. For these patients, oxygen administration for the correction of OSA-related nocturnal hypoxemia may reduce symptoms of OSA. Oxygen therapy has also been successfully used to treat central apneas as well, including Cheyne-Stokes respiration (CSR). In accordance with embodiments of the invention, a system controls gas therapy using one or more patient-internal sensors, one or more patient-external sensors, and/or an implanted device.

Gas therapy, such as oxygen therapy, continuous positive airway pressure therapy, or other therapies provided to a patient through the pulmonary system, may mitigate a patient's suffering from a number of respiratory disorders. Some lung diseases, such as emphysema, sarcoidosis, and chronic obstructive pulmonary disorder, reduce lung function to the extent that supplemental oxygen is needed to continue normal bodily functions. For many patients with end stage lung disease, oxygen therapy allows the patients to get the oxygen they need, helps them be more active, and may also prevent heart failure.

Gas therapy devices may be used to provide a variety of respiration therapies, including, for example, providing vasodilating agents, continuous positive airway pressure (CPAP), bi-level positive airway pressure (bi-level PAP), proportional positive airway pressure (PPAP), auto-titrating positive airway pressure, ventilation, gas or oxygen therapies. All types of gas therapy and positive airway pressure devices are referred to generically herein as xPAP devices.

Expired gases or blood gases may be used to adjust cardiac rhythm management (CRM) and/or xPAP therapies to provide more effective treatment of disordered breathing, a pulmonary disorder, and/or a cardiac disorder. The blood gas sensors may be implemented using either a patient-internal sensor or a patient-external sensor. Expired gases may be sensed using a patient-external sensor positioned, for example, on the respiratory mask of the xPAP device. The use of external sensors avoids the stability, reliability, and power consumption problems associated with implanted sensors. The use of implanted sensors resolves compliance issues common to xPAP therapy. The gas concentration in the expired air collected at the very end of expiration (just before inhalation starts) is representative of the blood gas concentration. This provides a non-invasive way of measuring blood gas concentrations.

The blood hydrogen ion concentration (or pH) is related to the relative amount of carbon dioxide and various chemical buffering agents in the blood. The blood pH is therefore closely influenced by respiration. The blood pH is related to the internal respiratory control and is therefore an important indicator of respiratory disorders, including apnea, COPD and others.

Various diseases and disorders, e.g., sleep apnea, are associated with various levels of expired respiratory gases and/or blood gases. The detection of changes in expired gases, blood gases, and/or blood pH may be used in connection with diagnosis of a variety of diseases. Further, expired gas, blood gas concentrations, and/or pH may be used to detect and/or predict episodes of disordered breathing, a pulmonary disorder, and/or a cardiac disorder. Further, detection of expired gas, blood gas concentrations, and/or blood pH may be used to initiate, terminate, or modify respiratory and cardiac therapy.

Embodiments of the invention are directed to systems and methods that acquire and process blood chemistry information in an implantable or partially implantable device. Information acquired from blood gas or pH sensors, for example, may be used in connection with patient monitoring, diagnosis, and therapy. An implantable system may incorporate expired gas, blood gas, and/or pH detection for various purposes, including disease diagnosis and therapy control, among other functions. The system may include one or more or expired gas, blood gas, and/or pH sensors, which may be implemented as one or more patient-internal and/or one or more patient-external sensors.

As referenced herein, the term "condition" denotes a parameter that may be sensed, measured, and/or otherwise discerned based on a signal generated by a sensor or other input device of the one or more medical devices. For example, a physiological sensor typically generates a signal modulated by a particular physiological parameter. In some cases, a physiological condition, as the term is used herein, may be directly measured based on the sensor signal. In other cases, a physiological condition measurement may be derived from the sensor signal.

The terms "symptom" and "physiological change" refer to a manifestation of a medical disease or disorder. Symptoms and/or physiological changes may be detectable based on a sensed presence of one or more physiological conditions and/or measured values associated with the one or more sensed physiological conditions. The terms "disease" and/or "disorder" are used to refer to a medical dysfunction that is characterizable by a collection of symptoms or physiological changes.

An example of a pH sensor suitable for implantation is described in U.S. Pat. No. 4,312,734, which is hereby incorporated herein by reference. An example of an oxygen sensor suitable for implantation is described in U.S. Pat. No. 4,390,405, which is hereby incorporated herein by reference.

The following discussion, with reference to FIGS. 1 through 5, describes embodiments of the invention involving measurement of expired gases, blood gases or blood pH used for diagnosis and therapy. The processes and systems exemplified by these embodiments may be implemented alone or in combination with one or more processes and systems exemplified by other embodiments described herein to provide a coordinated approach to patient monitoring, diagnosis, and/or therapy.

In accordance with embodiments of the invention, a system controls gas therapy, such as oxygen therapy, using one or more patient-internal sensors, one or more patient-external sensors, and/or an implanted device. The gas therapy may be delivered to the patient, and measurement of exhaled gas concentration may be implemented using a respiratory mask, such as a CPAP mask, for example. The one or more sensors may include, for example, a gas saturation sensor or other implanted sensor for determining the patient's blood gas saturation. The patient's blood gas saturation may be determined externally, e.g., using pulse oximetry techniques, and/or external sensors positioned on a respiratory mask or nasal cannulae.

Expired gases, blood gases, and/or pH may be used to adjust CRM and/or xPAP therapies to provide more effective treatment of disordered breathing, a pulmonary disorder, and/or a cardiac disorder. The blood gas or pH sensors may be implemented using either a patient-internal sensor or a patient-external sensor. Expired gases may be sensed using a patient-external sensor positioned, for example, on the mask of the xPAP device. The use of external sensors avoids the stability, reliability, and power consumption problems associated with implanted sensors. The use of implanted sensors resolves compliance issues common to xPAP therapy. The gas concentration in the expired air collected at the very end of expiration just before inhalation starts) is representative of the blood gas concentration. This provides a non-invasive way of measuring blood gas concentrations.

In accordance with embodiments of the invention, as is illustrated in FIG. 1A, a system 100 may be configured with one or more sensors 110 that are configured to sense one or more parameters influence by disordered breathing. The sensors 110 may be implemented as implantable sensors, patient-external sensors, or both implantable and patient-external sensors. A DB therapy controller 150 may be configured for implantable or patient-external operation. For example, the DB therapy controller 150 may be implemented as a controller of an xPAP device 130 or a controller of a cardiac rhythm management device 120. The DB therapy controller 150 detects disordered breathing using sense information received from the sensors 110, and adjusts therapies deliverable by the xPAP and CRM devices 130, 120 responsive to the sense information. Adjustment of xPAP and CRM therapies includes, for example, initiation, termination, or modification of such therapies.

Figure 1B:
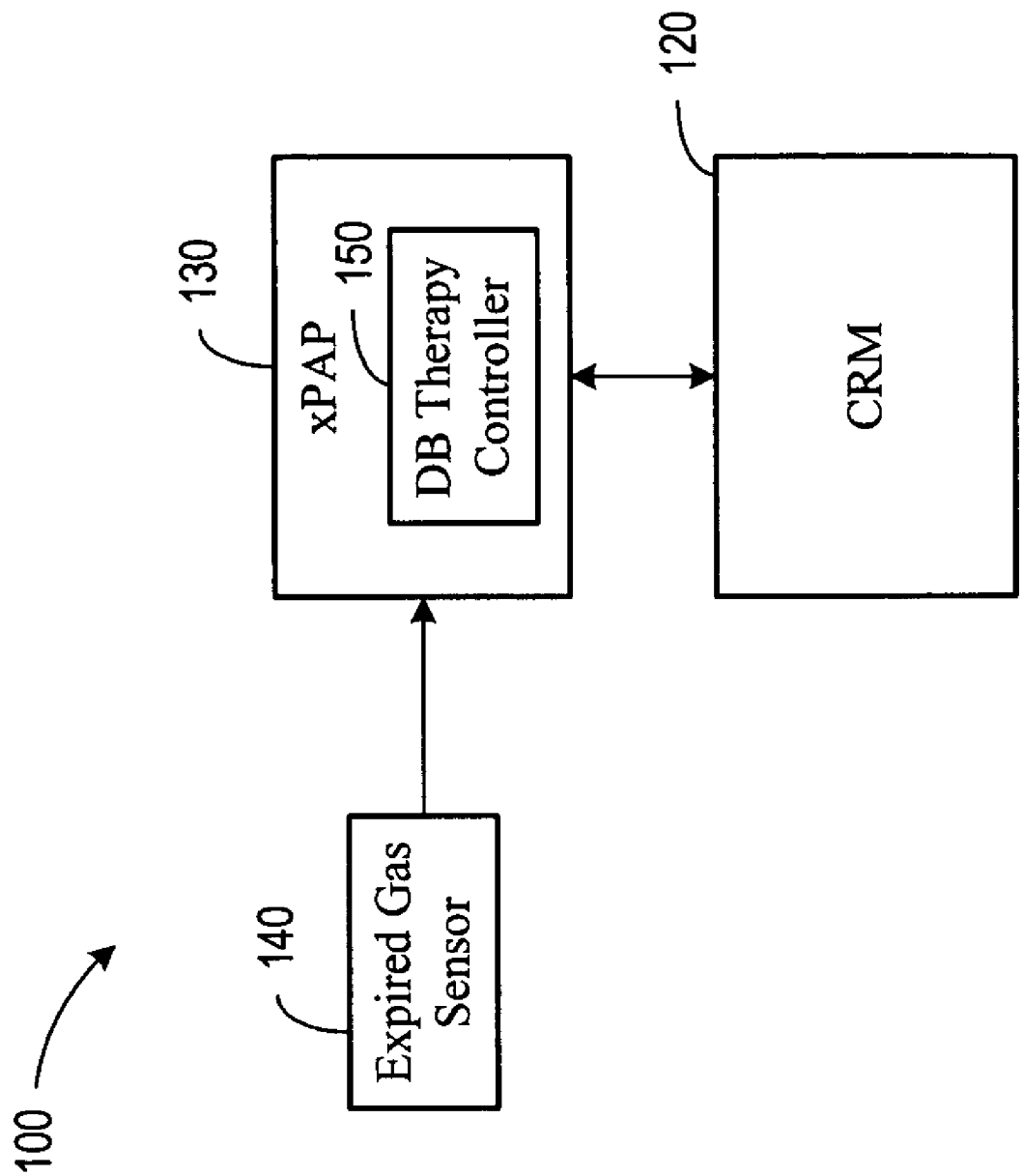
FIG. 1B is a block diagram of a system used to provide measurement of expired gases for diagnosis and therapy in accordance with embodiments of the invention.

In accordance with another embodiment of the invention, illustrated in FIG. 1B, a system 100 may be configured with a patient-external expired gas sensor 140 used to modify cardiac pacing therapy and respiratory therapy for treating disordered breathing, a pulmonary disorder, and/or a cardiac disorder. The expired gas sensor 140 may be positioned in an appropriate location on the mask of an xPAP device 130. In the embodiment illustrated in FIG. 1, the expired gas sensor 140 is coupled to the xPAP device 130. Expired gas concentration is measured at the end of expiration. A timing element (not shown) may be used to coordinate operations with the patient's respiration cycle to make the expired gas concentration measurement at the end of expiration.

The xPAP device 130 includes a disordered breathing (DB) therapy controller 150. The DB therapy controller 150 detects expired gas, e.g., expired oxygen, and compares concentration of the expired gas to a predetermined threshold or range. When the gas concentration is beyond the threshold or range, the DB therapy controller 150 may initiate, terminate, or modify a respiratory therapy provided by the xPAP device 130. Further, the DB therapy controller 150 may communicate with a CRM device 120, e.g., through a wireless communication link or other communications mechanism, to initiate, terminate, or modify the electrical stimulation therapy provided by the CRM device 120.

Figure 2:
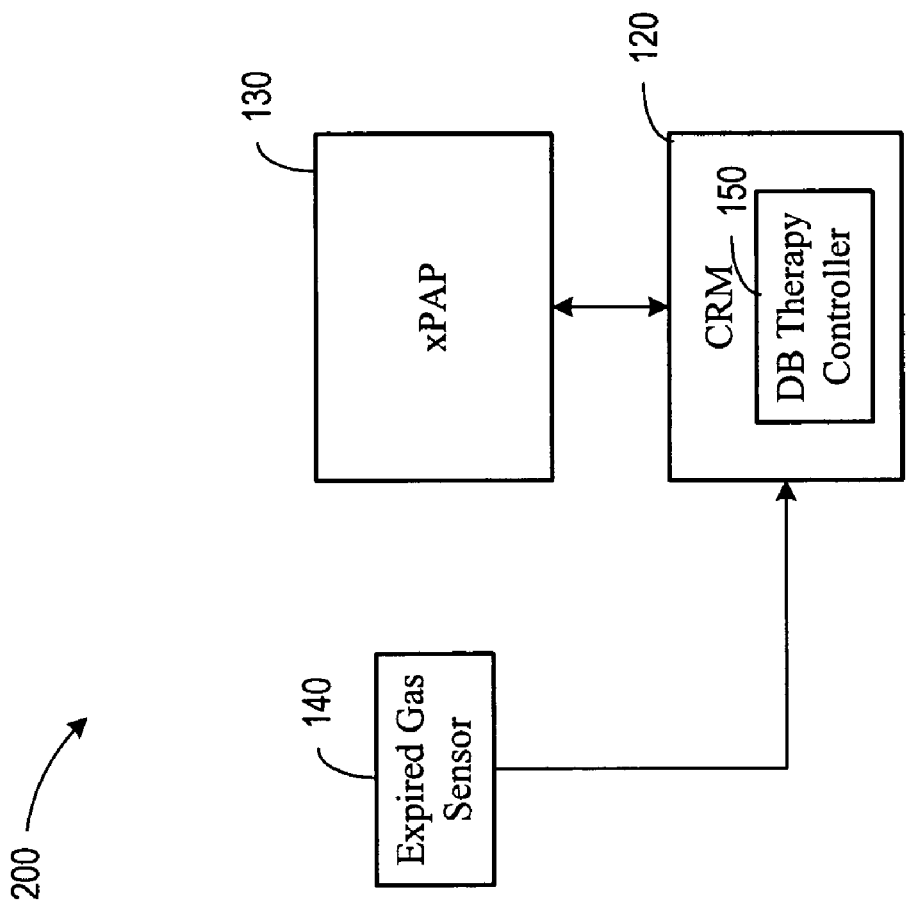
FIG. 2 is a block diagram illustrating a system for diagnosis and/or therapy using measurement of expired gases in accordance with embodiments of the invention.

In another embodiment of the invention, illustrated in FIG. 2, a system 200 includes the DB therapy controller 150 located within the CRM device 120. The external expired gas sensor 140 may wirelessly transmit to the CRM device 120 sensed signals associated with expired gas concentration. The DB therapy controller 150 compares the concentration of the expired gas to a predetermined threshold or range. When the gas concentration is beyond the threshold or range, the DB therapy controller 150 may initiate, terminate, or modify an electrical stimulation therapy provided by the CRM device 120. Further, the DB therapy controller 150 may communicate with the xPAP device 130, e.g., through a wireless communication link or other communications mechanism, to initiate, terminate, or modify a respiratory therapy provided by the xPAP device 130.

Figure 3:
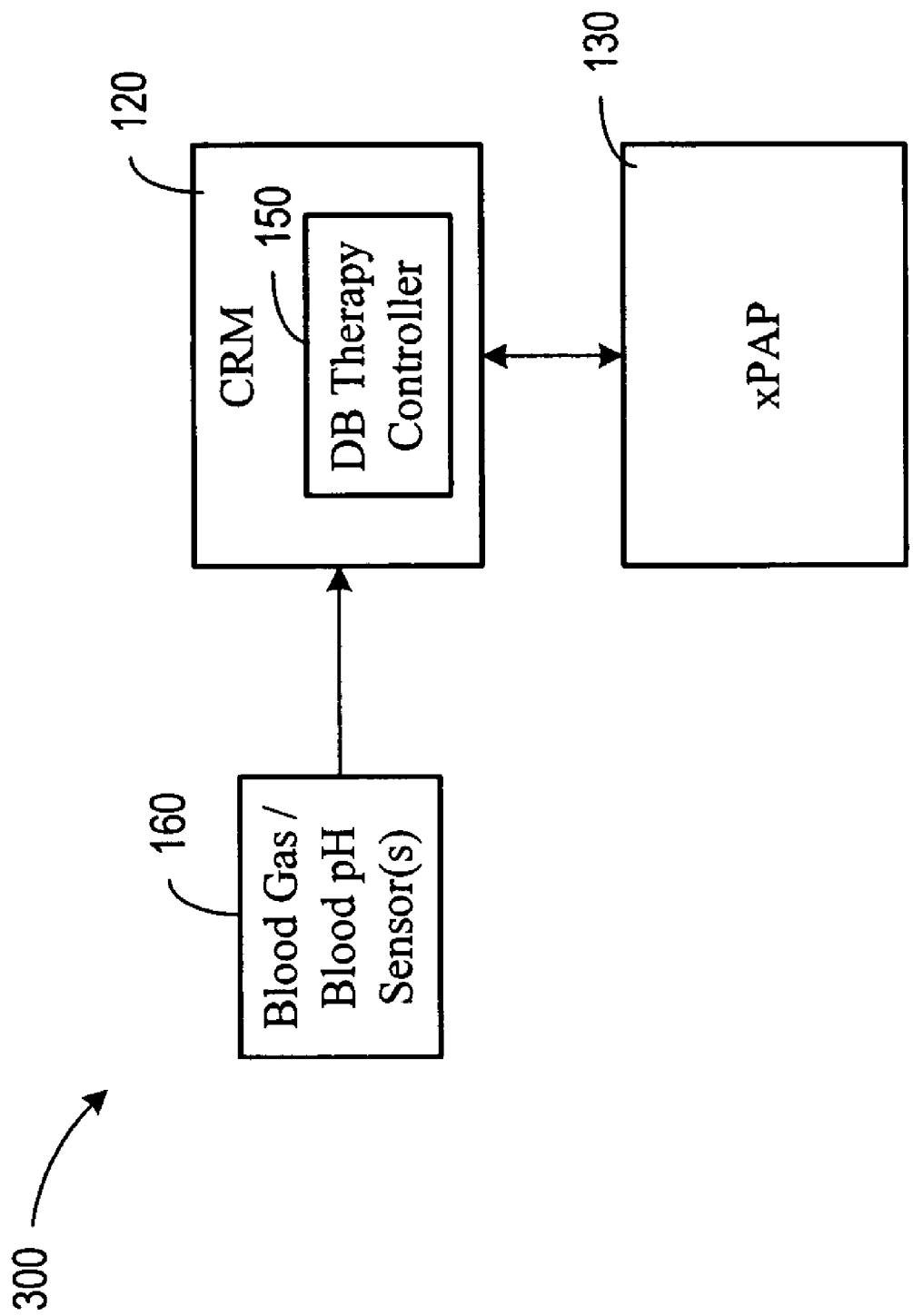
FIG. 3 is a block diagram illustrating a system for diagnosis and/or therapy using measurement of blood gases/blood pH in accordance with further embodiments of the invention.

In accordance with yet another embodiment of the invention, illustrated in FIG. 3, a system 300 includes an implanted blood sensor 160 that provides information used to modify cardiac pacing therapy and respiratory therapy for disordered breathing, a pulmonary disorder, and/or a cardiac disorder. The implanted blood sensor 160 may include one or both of a blood gas sensor or a blood pH sensor. For example, the blood sensor 160 may be configured to sense one or more of blood oxygen concentration, blood carbon dioxide concentration, or blood pH.

The blood sensor 160 may be positioned, for example, on an endocardiac lead implanted in a chamber of the patient's heart and coupled to the CRM device 120. The CRM device 120 in this example includes, or otherwise incorporates the functionality of, the DB therapy controller 150. The DB therapy controller 150 may detect blood gas concentration, e.g., blood oxygen and/or carbon dioxide concentration, and compare concentration of the blood gas to a predetermined threshold or range. When the blood gas concentration is beyond the threshold or range, the DB therapy controller 150 may initiate, terminate, or modify the electrical stimulation therapy provided by the CRM device 120. Further, the DB therapy controller 150 may communicate with the xPAP device 130, e.g., through a wireless communication link or other communications mechanism, to initiate, terminate, or modify the respiratory therapy provided by the xPAP device 130. An equivalent to the above example could be implemented using a blood pH sensor or a combination of blood gas and blood pH sensors.

Figure 4:
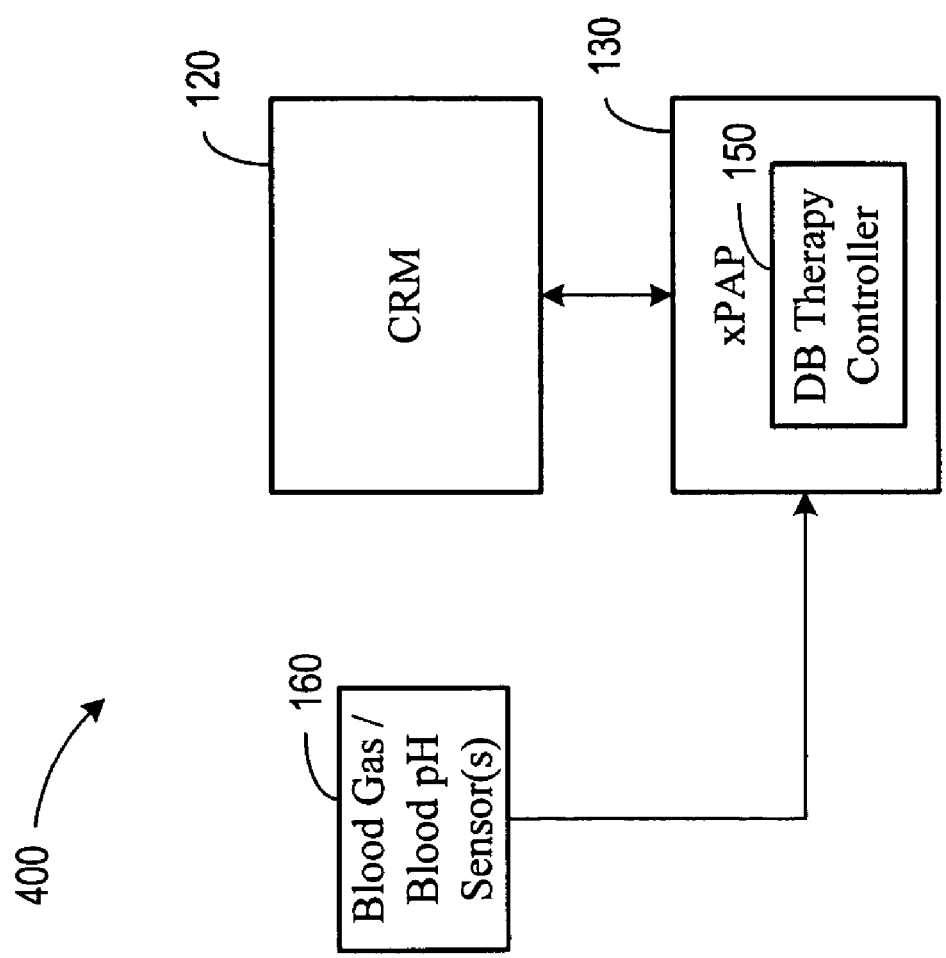
FIG. 4 is a block diagram illustrating a system for diagnosis and/or therapy using measurement of blood gases/blood pH in accordance with embodiments of the invention.

In another embodiment, illustrated in FIG. 4, a system 400 includes the DB therapy controller 150 within the xPAP device 130. The blood sensor 160 may wirelessly transmit to the xPAP device 130 sensed signals associated with blood gas concentration and/or blood pH. The DB therapy controller 150 compares the concentration of the expired gas to a predetermined threshold or range. When the gas concentration is beyond the threshold or range, the DB therapy controller 150 may initiate, terminate, or modify the respiratory therapy provided by the xPAP device 130. Further, the DB therapy controller 150 may communicate with the CRM device 120, e.g., through a wireless communication link or other communications mechanism, to initiate, terminate, or modify the electrical stimulation therapy provided by the CRM device 120. An equivalent to the above example could be implemented using a blood pH sensor or a combination of blood gas and blood pH sensors.

As is illustrated in the examples shown in FIGS. 1 through 4, many possible combinations of componentry and nesting or combinations of componentry are possible in accordance with the present invention. The specific configurations shown in FIGS. 1 through 4 are four non-limiting examples of possible configurations of systems in accordance with the present invention.

Figure 5:
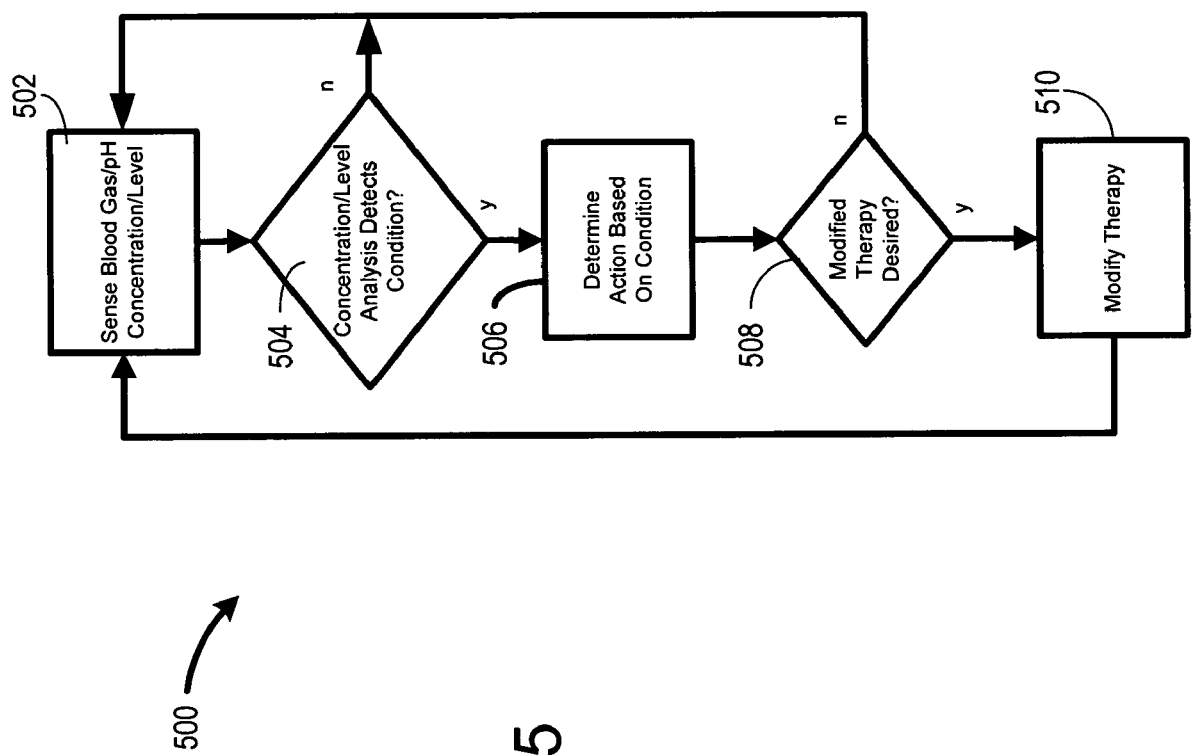
FIG. 5 is a flow chart illustrating a method of diagnosis and/or therapy in accordance with embodiments of the invention.

FIG. 5 is a flow chart illustrating a method 500 of therapy control based on signals from a patient-internal device in accordance with embodiments of the invention. The method 500 may be useful for controlling systems using combined gas and cardiac therapies, such as those illustrated with reference to FIGS. 1 through 4. For clarity of understanding, and not by way of limitation, the sensing of blood oxygen level and/or blood pH will be used as an example of one use of the method 500. For example, an equivalent embodiment could be implemented using blood carbon dioxide level.

Block 502 provides for the sensing of a blood chemistry parameter, such as blood gas concentration (e.g., blood oxygen level or blood carbon dioxide level) and/or blood pH. An analysis 504 is made of the sensed blood gas concentration and/or blood pH. For example, a blood oxygen and/or pH level may be compared to a range of acceptable levels to detect whether the blood gas concentration/pH is within an acceptable range, or whether some disease/disorder is diagnosable. If blood oxygen/pH level is acceptable and no disease/disorder is diagnosed at analysis 504, the blood gas/pH sensing continues at block 502. Sensing may occur continuously, intermittently, by-request, periodically, or as otherwise desired.

If a disease/disorder is detected at analysis 504, a determination 506 is made, relative to the detected disease/disorder. For example, detecting a blood oxygen below a lower threshold may suggest that more oxygen is needed by the patient. A decision 508 is made as to whether some modifications and/or therapies are desired to increase the blood oxygen level. For example, if a patient is receiving oxygen therapy and cardiac pacing, the oxygen level administered to the patient may be adjusted and the heart rate may be adjusted. In another embodiment, if the patient is sleeping and wearing a CPAP device, the air pressure may be increased and the heart rate may be increased. In a further embodiment, the patient may be administered a vasodilating agent, or have a level of vasodilating agent therapy modified along with adjustment of the heart rate. Combined therapies may also be performed, such as increasing gas pressure and adding a vasodilating agent, or other desired therapy combination.

If no therapy change is desired, the presence of the disease/disorder may be recorded and monitored, and/or an alert signal may be generated responsive to the detection of the disease/disorder, for example, before returning to the sense block 502. If a therapy change is desired, the therapy is modified at a block 510 before again returning to the blood sense block 502. For example, if a patient is receiving oxygen therapy, the oxygen level administered to the patient is increased, and the method 500 may be performed again after an appropriate time to determine if the change was effective, or whether other action is necessary.

Information about the patient's blood gas and/or pH levels may be used to enhance sleep monitoring and/or diagnosis of a variety of disorders. Detection of blood gas level and/or pH may be used to diagnose disorders as well as trigger the sleep-time therapy in a respiratory and cardiac device. Data acquired during sleep may assist in diagnosing various sleep-related disorders. The collected data may be stored, displayed, printed, or transmitted to a separate device.

Figure 6:
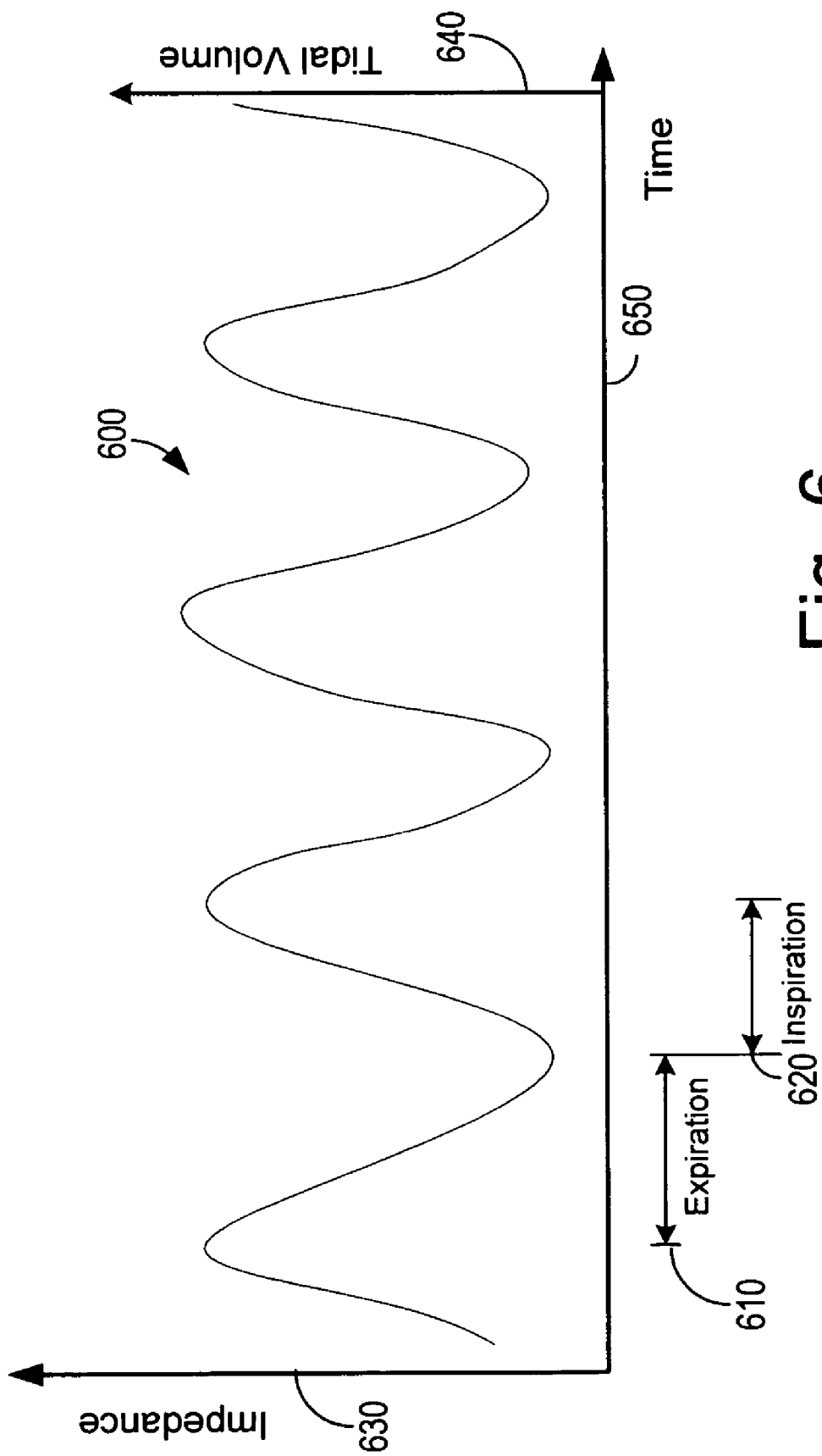
FIG. 6 is a graph of a normal respiration signal measured by a transthoracic impedance sensor that may be utilized for coordinated monitoring, diagnosis, and/or therapy in accordance with embodiments of the invention.

Referring now to FIG. 6, an impedance signal 600 is illustrated. The impedance signal 600 may be developed, for example, from an impedance sense electrode in combination with a CRM device. The impedance signal 600 is proportional to the transthoracic impedance, illustrated as an impedance 630 on the abscissa of the left side of the graph in FIG. 6.

The impedance 630 increases during any respiratory inspiration 620 and decreases during any respiratory expiration 610. The impedance signal 600 is also proportional to the amount of air inhaled, denoted by a tidal volume 640, illustrated on the abscissa of the right side of the graph in FIG. 6. The variations in impedance during respiration, identifiable as the peak-to-peak variation of the impedance signal 600, may be used to determine the respiration tidal volume 640. Tidal volume 640 corresponds to the volume of air moved in a breath, one cycle of expiration 610 and inspiration 620. A minute-ventilation may also be determined, corresponding to the amount of air moved per a minute of time 650 illustrated on the ordinate of the graph in FIG. 6.

Arousal and other episodes of breathing disorders may be determined using the impedance signal 630. During non-REM sleep, a normal respiration pattern includes regular, rhythmic inspiration—expiration cycles without substantial interruptions. When the tidal volume (TV) of the patient's respiration, as indicated by the transthoracic impedance signal, falls below a hypopnea threshold, then a hypopnea event is declared. For example, a hypopnea event may be declared if the patient's tidal volume falls below about 50% of a recent average tidal volume or other baseline tidal volume value. If the patient's tidal volume falls further to an apnea threshold, e.g., about 10% of the recent average tidal volume or other baseline value, an apnea event is declared.

Figure 7A:
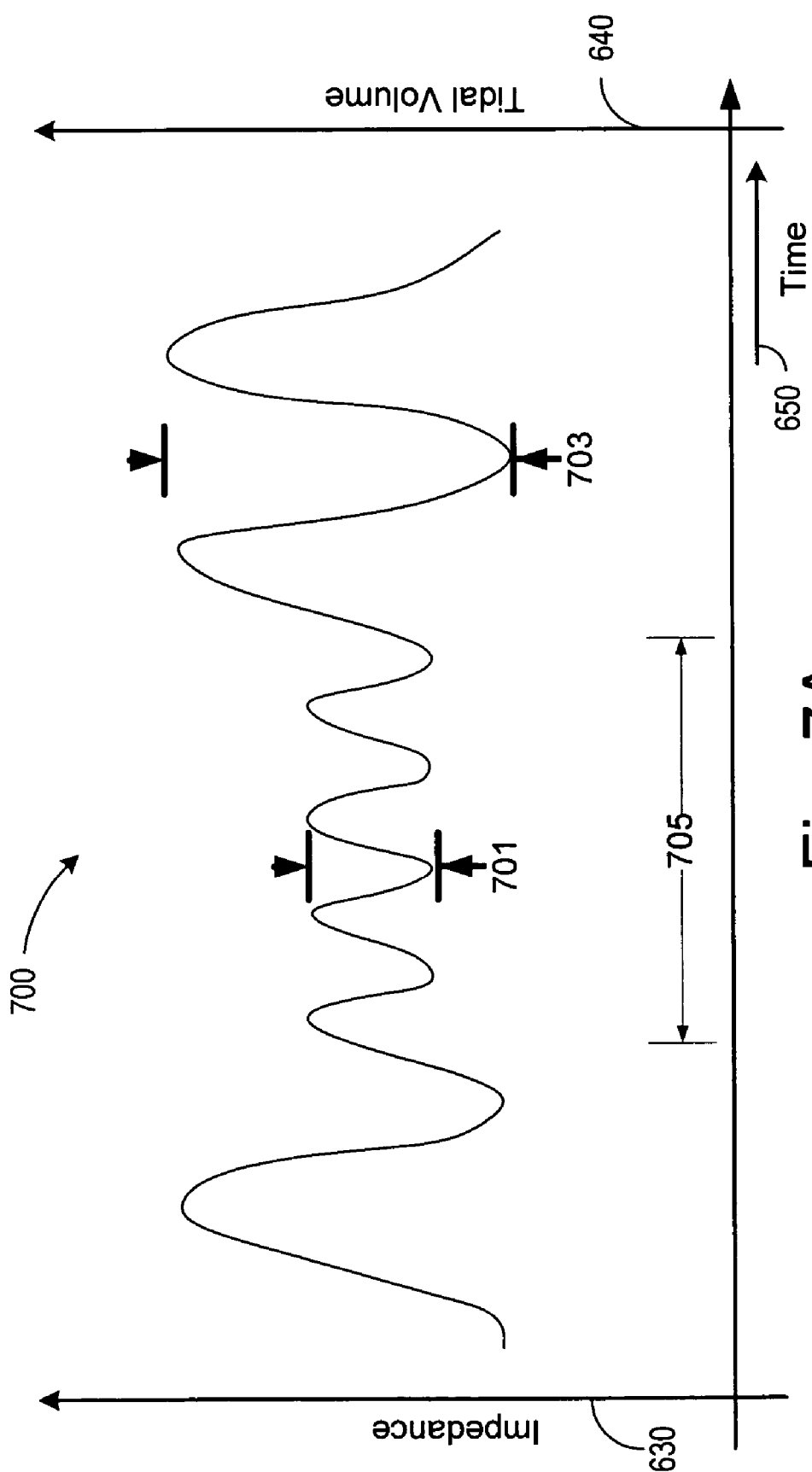
FIG. 7A is a respiration graph illustrating abnormally shallow respiration utilized in detection of disordered breathing, a pulmonary disorder, and/or a cardiac disorder in accordance with embodiments of the invention.

Hypopnea is a type of disordered breathing characterized by abnormally shallow breathing. FIG. 7A is a graph of a tidal volume 700 derived from transthoracic impedance measurements. The graph of FIG. 7A illustrating the tidal volume 700 of a hypopnea episode may be compared to the tidal volume of a normal breathing cycle illustrated previously in FIG. 6, which illustrated the normal respiration tidal volume and rate. As shown in FIG. 7A, hypopnea involves a period of abnormally shallow respiration, possible at an increased respiration rate.

Hypopnea is detected by comparing a patient's respiratory tidal volume 703 to a hypopnea tidal volume 701. The tidal volume for each respiration cycle may be derived from transthoracic impedance measurements acquired in the manner described previously. The hypopnea tidal volume threshold may be established by, for example, using clinical results providing a representative tidal volume and duration of hypopnea events. In one configuration, hypopnea is detected when an average of the patient's respiratory tidal volume taken over a selected time interval falls below the hypopnea tidal volume threshold. Furthermore, various combinations of hypopnea cycles, breath intervals, and non-breathing intervals may be used to detect hypopnea, where the non-breathing intervals are determined as described above.

In FIG. 7A, a hypopnea episode 705 is identified when the average tidal volume is significantly below the normal tidal volume. In the example illustrated in FIG. 7A, the normal tidal volume during the breathing process is identified as the peak-to peak value identified as the respiratory tidal volume 703. The hypopnea tidal volume during the hypopnea episode 705 is identified as hypopnea tidal volume 701. For example, the hypopnea tidal volume 701 may be about 50% of the respiratory tidal volume 703.

The value 50% is used by way of example only, and determination of thresholds for hypopnea events may be determined as any value appropriate for a given patient. In the example above, if the tidal volume falls below 50% of the respiratory tidal volume 703, the breathing episode may be identified as a hypopnea event, originating the measurement of the hypopnea episode 705.

Figure 7B:
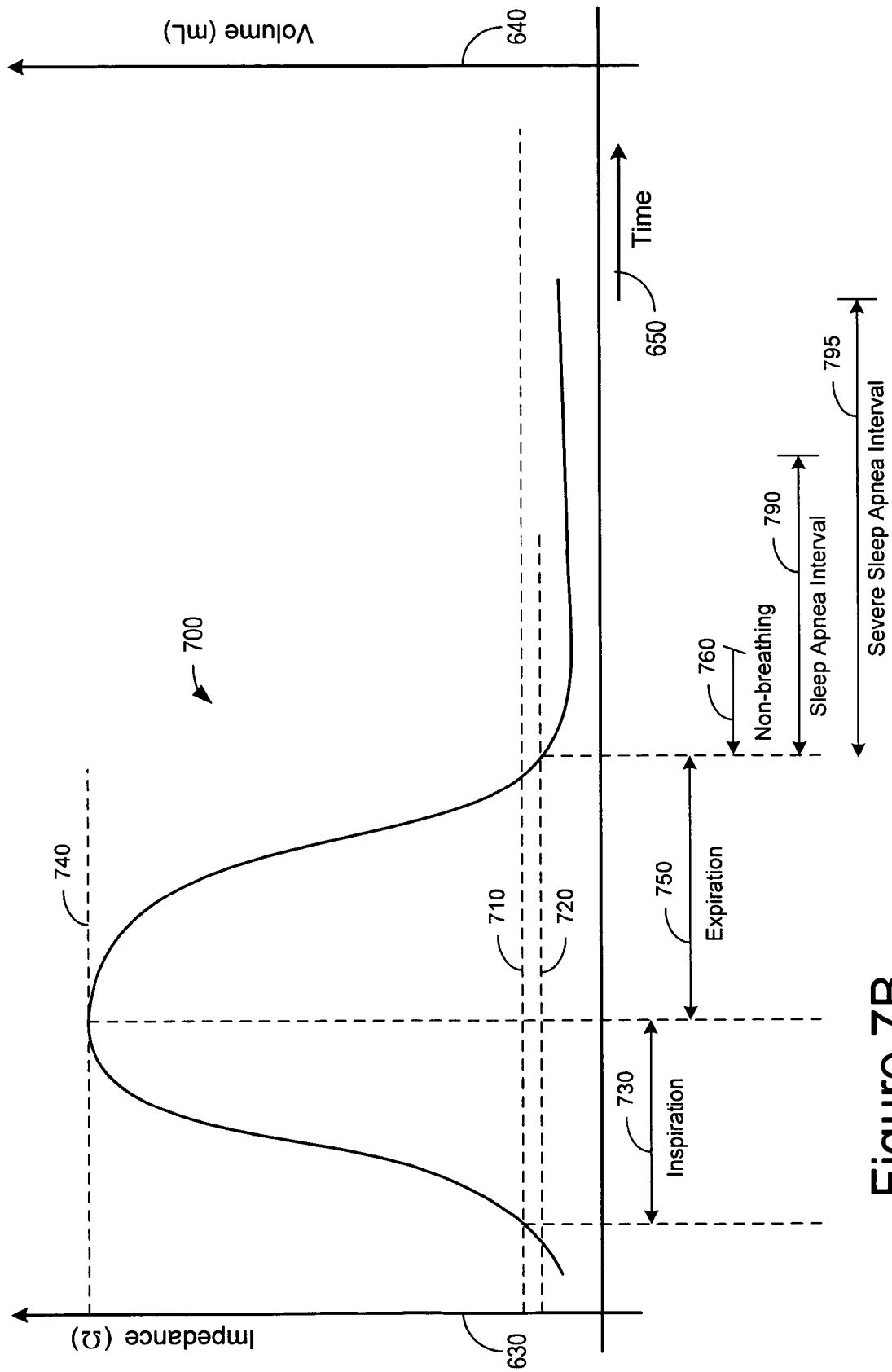
FIG. 7B is a respiration graph illustrating detection of sleep apnea in accordance with embodiments of the invention.

Detection of sleep apnea and severe sleep apnea is illustrated in FIG. 7B. The patient's respiration signals are monitored and the respiration cycles are defined according to an inspiration 730, an expiration 750, and a non-breathing 760 interval. Respiration intervals are established using inspiration 710 and expiration 720 thresholds. The inspiration threshold 710 marks the beginning of an inspiration period 730 and is determined by the transthoracic impedance signal rising above the inspiration threshold 710. The inspiration period 730 ends when the transthoracic impedance signal is maximum 740. A maximum transthoracic impedance signal 740 corresponds to both the end of the inspiration interval 730 and the beginning of the expiration interval 750. The expiration interval 750 continues until the transthoracic impedance falls below an expiration threshold 720. A non-breathing interval 760 starts from the end of the expiration period 750.

Sleep apnea is detected when a non-breathing period 760 exceeds a first predetermined interval 790, denoted the sleep apnea interval. Severe sleep apnea is detected when the non-breathing period 760 exceeds a second predetermined interval 795, denoted the severe sleep apnea interval. For example, sleep apnea may be detected when the non-breathing interval exceeds about 10 seconds, and severe sleep apnea may be detected when the non-breathing interval exceeds about 20 seconds.

Figure 8:
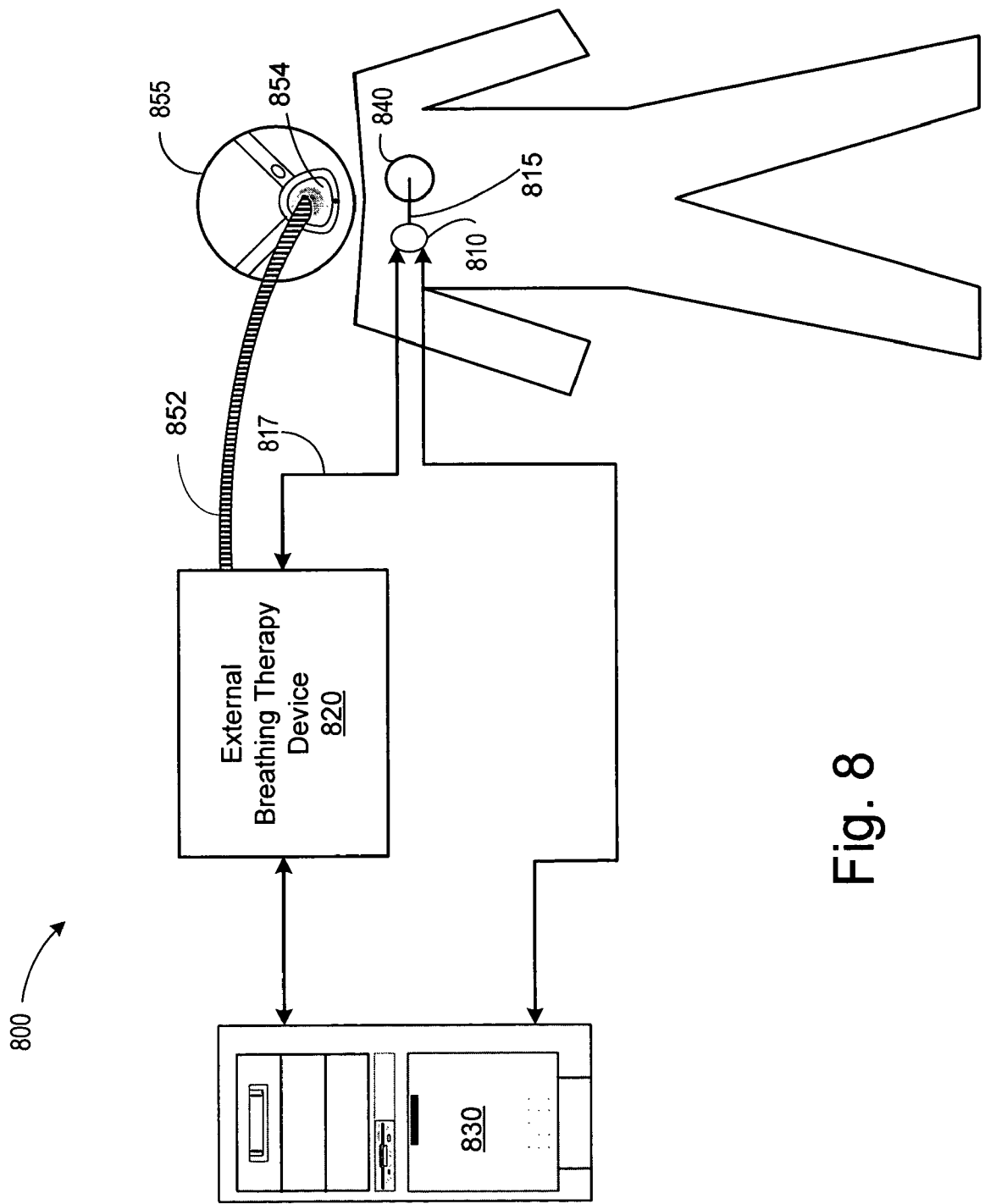
FIG. 8 illustrates a medical system including an implantable cardiac rhythm management device that cooperates with a patient-external respiration therapy device to provide coordinated patient monitoring, diagnosis and/or therapy in accordance with an embodiment of the invention.

According to one embodiment of the invention, illustrated in FIG. 8, a medical system 800 may include an implantable cardiac rhythm management device (CRM) 810 that cooperates with a patient-external respiration therapy device 820 to provide coordinated patient monitoring, diagnosis, and/or therapy. The CRM 810 may provide a first set of monitoring, diagnostic, and/or therapeutic functions to a patient 855. The CRM 810 may be electrically coupled to a patient's heart 840 through one or more cardiac electrodes 815 terminating in, on, or about the heart 840.

The cardiac electrodes 815 may sense cardiac signals produced by the heart 840 and/or provide therapy to one or more heart chambers. For example, the cardiac electrodes 815 may deliver electrical stimulation to one or more heart 840 chambers, and/or to one or multiple sites within the heart 840 chambers. The CRM 810 may directly control delivery of one or more cardiac therapies, such as cardiac pacing, defibrillation, cardioversion, cardiac resynchronization, and/or other cardiac therapies, for example. In addition, the CRM 810 may facilitate the control of a mechanical respiration device 820. Further, the CRM 810 may perform various monitoring and/or diagnostic functions in relation to the cardiovascular system and/or other physiological systems.

In the example illustrated in FIG. 8, a mechanical respiration therapy device 820 includes a positive airway pressure device that cooperates with a CRM 810. The xPAP device 820 develops a positive air pressure that is delivered to the patient's airway through a tube system 852 and a mask 854 connected to the xPAP device 820. Positive airway pressure devices are often used to treat disordered breathing. In one configuration, for example, the positive airway pressure provided by the xPAP device 820 acts as a pneumatic splint keeping the patient's airway open and reducing the severity and/or number of occurrences of disordered breathing due to airway obstruction.

The xPAP device 820 may directly control the delivery of respiration therapy to the patient, and may contribute to the control of the CRM device 810. In addition, the xPAP device 820 may provide a number of monitoring and/or diagnostic functions in relation to the respiratory system and/or other physiological systems.

The CRM 810 and xPAP device 820 may communicate directly through a wireless communications link 817, for example. Alternatively, or additionally, the CRM 810 and xPAP device 820 may communicate with and/or through an APM such as the APM system 830, as may be described further below with reference to FIG. 12.

Although FIG. 8 illustrates a CRM device 810 used with a xPAP device 820 to provide coordinated patient monitoring, diagnosis, and/or therapy, any number of patient-internal and patient-external medical devices may be included in a medical system in accordance with the invention. For example, a drug delivery device, such as a drug pump or controllable nebulizer, may be included in the system 800. The drug delivery device may cooperate with either or both of the CRM device 810 and the xPAP device 820 and may contribute to the patient monitoring, diagnosis, and/or therapeutic functions of the medical system 800.

Figure 9:
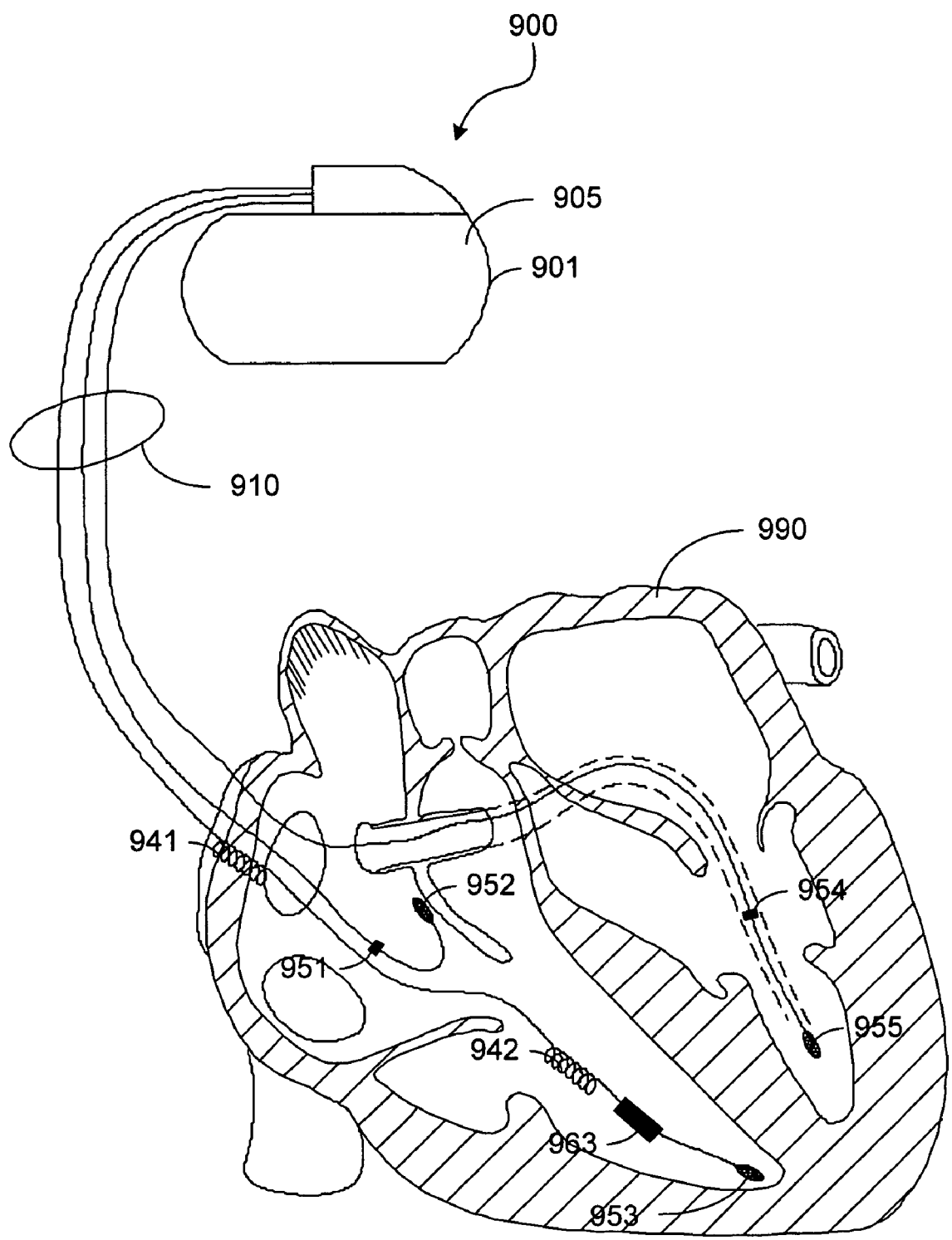
FIG. 9 is an illustration of an implantable cardiac device including a lead assembly shown implanted in a sectional view of a heart, the device used for coordinated patient monitoring, diagnosis, and/or therapy in accordance with embodiments of the invention.

FIG. 9 is a partial view of an implantable device useful for combined cardiac and respiratory therapies in accordance with embodiments of the invention. In this example, the implantable device comprises a cardiac rhythm management device (CRM) 900 including an implantable pulse generator 905 electrically and physically coupled to an intracardiac lead system 910. Portions of the intracardiac lead system 910 are inserted into the patient's heart 990. The intracardiac lead system 910 includes one or more electrodes configured to sense electrical cardiac activity of the heart, deliver electrical stimulation to the heart, sense the patient's transthoracic impedance, and/or sense other physiological parameters, e.g., cardiac chamber pressure or temperature. Portions of the housing 901 of the pulse generator 905 may optionally serve as a can electrode.

Communications circuitry is disposed within the housing 901 for facilitating communication between the pulse generator 905 and an external communication device, such as a portable or bed-side communication station, patient-carried/worn communication station, or external programmer, for example. The communications circuitry can also facilitate unidirectional or bidirectional communication with one or more implanted, external, cutaneous, or subcutaneous physiologic or non-physiologic sensors, patient-input devices and/or information systems.

The pulse generator 905 may optionally incorporate a motion detector that may be used to sense various respiration-related conditions. For example, the motion detector may be optionally configured to sense snoring, activity level, and/or chest wall movements associated with respiratory effort, for example. The motion detector may be implemented as an accelerometer positioned in or on the housing 901 of the pulse generator 905. If the motion sensor is implemented as an accelerometer, the motion sensor may also provide respiratory, e.g. rales, coughing, and cardiac, e.g. S1-S4 heart sounds, murmurs, and other acoustic information.

The lead system 910 of the CRM 900 may incorporate one or more transthoracic impedance sensors that may be used to acquire the patient's respiration waveform, or other respiration-related information. The transthoracic impedance sensor may include, for example, one or more intracardiac electrodes 941, 942, 951-955, 963 positioned in one or more chambers of the heart 990. The intracardiac electrodes 941, 942, 951-955, 963 may be coupled to impedance drive/sense circuitry positioned within the housing of the pulse generator 905.

In one implementation, impedance drive/sense circuitry generates a current that flows through the tissue between an impedance drive electrode 951 and a can electrode on the housing 901 of the pulse generator 905. The voltage at an impedance sense electrode 952 relative to the can electrode changes as the patient's transthoracic impedance changes. The voltage signal developed between the impedance sense electrode 952 and the can electrode is detected by the impedance sense circuitry. Other locations and/or combinations of impedance sense and drive electrodes are also possible.

The voltage signal developed at the impedance sense electrode 952 is proportional to the patient's transthoracic impedance and represents the patient's respiration waveform. The transthoracic impedance increases during respiratory inspiration and decreases during respiratory expiration. The peak-to-peak transition of the transthoracic impedance is proportional to the amount of air moved in one breath, denoted the tidal volume. The amount of air moved per minute is denoted the minute ventilation. A normal "at rest" respiration pattern, e.g., during non-REM sleep, includes regular, rhythmic inspiration—expiration cycles without substantial interruptions.

The lead system 910 may include one or more cardiac pace/sense electrodes 951-955 positioned in, on, or about one or more heart chambers for sensing electrical signals from the patient's heart 990 and/or delivering pacing pulses to the heart 990. The intracardiac sense/pace electrodes 951-955, such as those illustrated in FIG. 9, may be used to sense and/or pace one or more chambers of the heart, including the left ventricle, the right ventricle, the left atrium and/or the right atrium. The lead system 910 may include one or more defibrillation electrodes 941, 942 for delivering defibrillation/cardioversion shocks to the heart. The pulse generator 905 may include circuitry for detecting cardiac arrhythmias and/or for controlling pacing or defibrillation therapy in the form of electrical stimulation pulses or shocks delivered to the heart through the lead system 910 to treat the detected arrhythmias.

Figure 10:
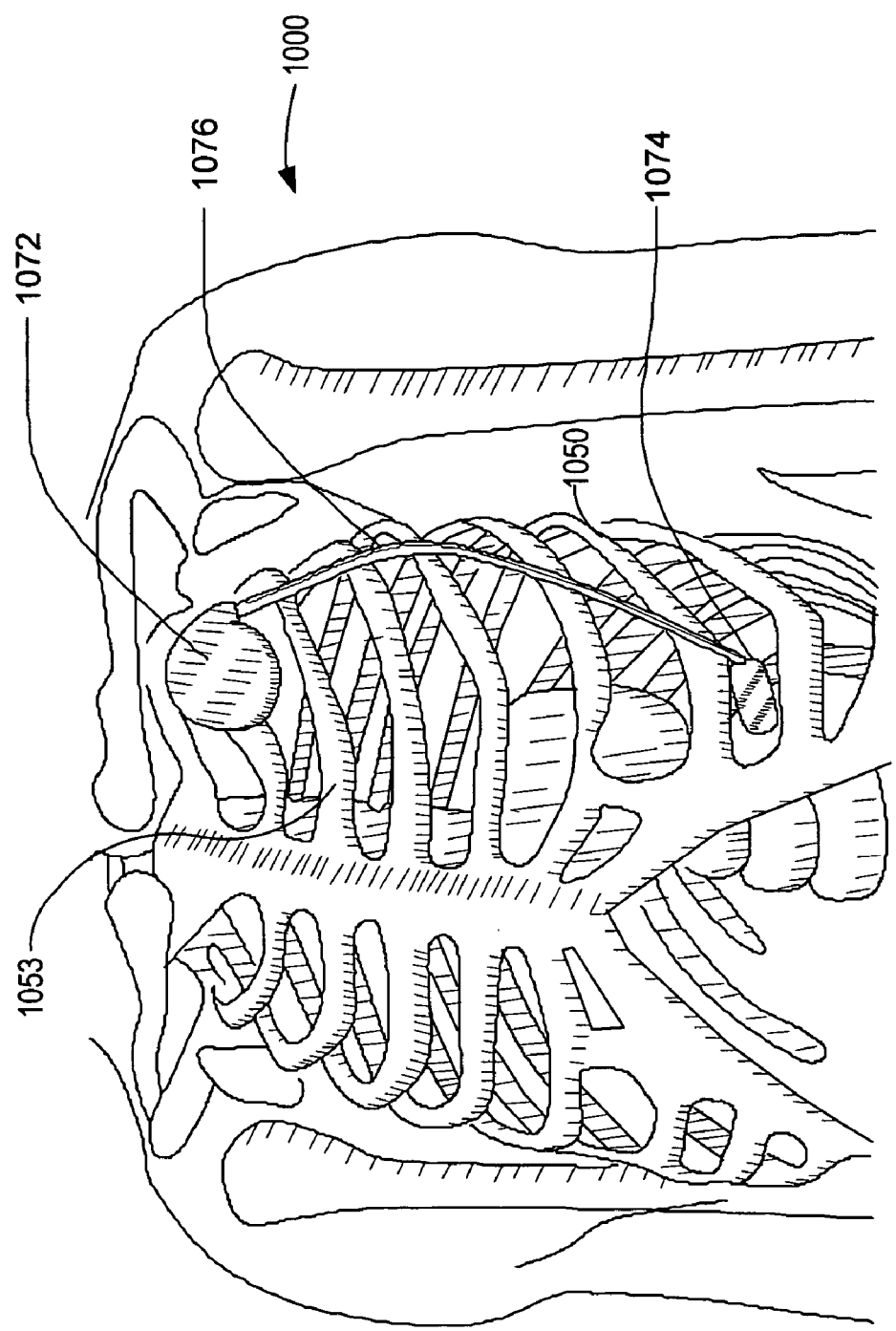
FIG. 10 is an illustration of a thorax having an implanted subcutaneous medical device that may be used for coordinated patient monitoring, diagnosis, and/or therapy in accordance with an embodiment of the invention.

FIG. 10 is a diagram illustrating a subcutaneous implantable medical device 1000 that may be used for diagnosis and therapy using measurement of expired gases and/or blood gases or blood pH in accordance with embodiments of the invention. The device 1000 illustrated in FIG. 10 is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

The primary housing (e.g., the active or non-active can) of the ITCS device, for example, may be configured for positioning outside of a rib cage 1050 at an intercostal or subcostal location, within the abdomen, or in the upper chest region (e.g., subclavian location, such as above a third rib 1053). In one implementation, one or more electrodes may be located on a primary housing 1072 and/or at other locations about, but not in direct contact with the heart, great vessel or coronary vasculature.

In the particular configuration shown in FIG. 10, the ITCS device includes the housing 1072 within which various cardiac sensing, detection, processing, and energy delivery circuitry may be housed. It is understood that the components and functionality depicted in the figures and described herein may be implemented in hardware, software, or a combination of hardware and software. It is further understood that the components and functionality depicted as separate or discrete blocks/elements in the figures in general may be implemented in combination with other components and functionality, and that the depiction of such components and functionality in individual or integral form is for purposes of clarity of explanation, and not of limitation.

Communications circuitry may be disposed within the housing 1072 for facilitating communication between the ITCS device and an external therapy device as is illustrated in FIGS. 1 through 4, as well as other devices, such as a portable or bed-side communication station, patient-carried/worn communication station, or external programmer, for example. The communications circuitry may also facilitate unidirectional or bidirectional communication with one or more external, cutaneous, or subcutaneous physiologic or non-physiologic sensors. The housing 1072 is typically configured to include one or more electrodes (e.g., can electrode and/or indifferent electrode). Although the housing 1072 is typically configured as an active can, it is appreciated that a non-active can configuration may be implemented, in which case at least two electrodes spaced apart from the housing 1072 are employed.

In the configuration shown in FIG. 10, a subcutaneous electrode 1074 may be positioned under the skin in the chest region and situated distal from the housing 1072. The subcutaneous and, if applicable, housing electrode(s) may be positioned about the heart at various locations and orientations, such as at various anterior and/or posterior locations relative to the heart. The subcutaneous electrode 1074 is coupled to circuitry within the housing 1072 via a lead assembly 1076. One or more conductors (e.g., coils or cables) are provided within the lead assembly 1076 and electrically couple the subcutaneous electrode 1074 with circuitry in the housing 1072. One or more sense, sense/pace or defibrillation electrodes may be situated on the elongated structure of the electrode support, the housing 1072, and/or the distal electrode assembly (shown as subcutaneous electrode 1074 in the configuration shown in FIG. 10).

In one configuration, the electrode support assembly and the housing 1072 define a unitary structure (e.g., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure may have an arcuate or angled shape, for example.

According to another configuration, the electrode support assembly defines a physically separable unit relative to the housing 1072. The electrode support assembly includes mechanical and electrical couplings that facilitate mating engagement with corresponding mechanical and electrical couplings of the housing 1072. For example, a header block arrangement may be configured to include both electrical and mechanical couplings that provide for mechanical and electrical connections between the electrode support assembly and housing 1072. The header block arrangement may be provided on the housing 1072 or the electrode support assembly. Alternatively, a mechanical/electrical coupler may be used to establish mechanical and electrical connections between the electrode support assembly and housing 1072. In such a configuration, a variety of different electrode support assemblies of varying shapes, sizes, and electrode configurations may be made available for physically and electrically connecting to a standard ITCS device housing 1072.

Various embodiments described herein may be used in connection with subcutaneous monitoring, diagnosis, and/or therapy. Methods, structures, and/or techniques described herein relating to subcutaneous systems and methods may incorporate features of one or more of the following commonly owned US Patent Applications: "Subcutaneous Cardiac Sensing, Stimulation, Lead Delivery, and Electrode Fixation Systems and Methods," Ser. No. 60/462,272, filed Apr. 11, 2003 and now expired; "Reconfigurable Subcutaneous Cardiac Device," published as U.S. Patent Application Publication 2004/0215240 now abandoned; and "Subcutaneous Cardiac Rhythm Management," U.S. Pat. No. 7,570,997; each hereby incorporated herein by reference.

Figure 11:
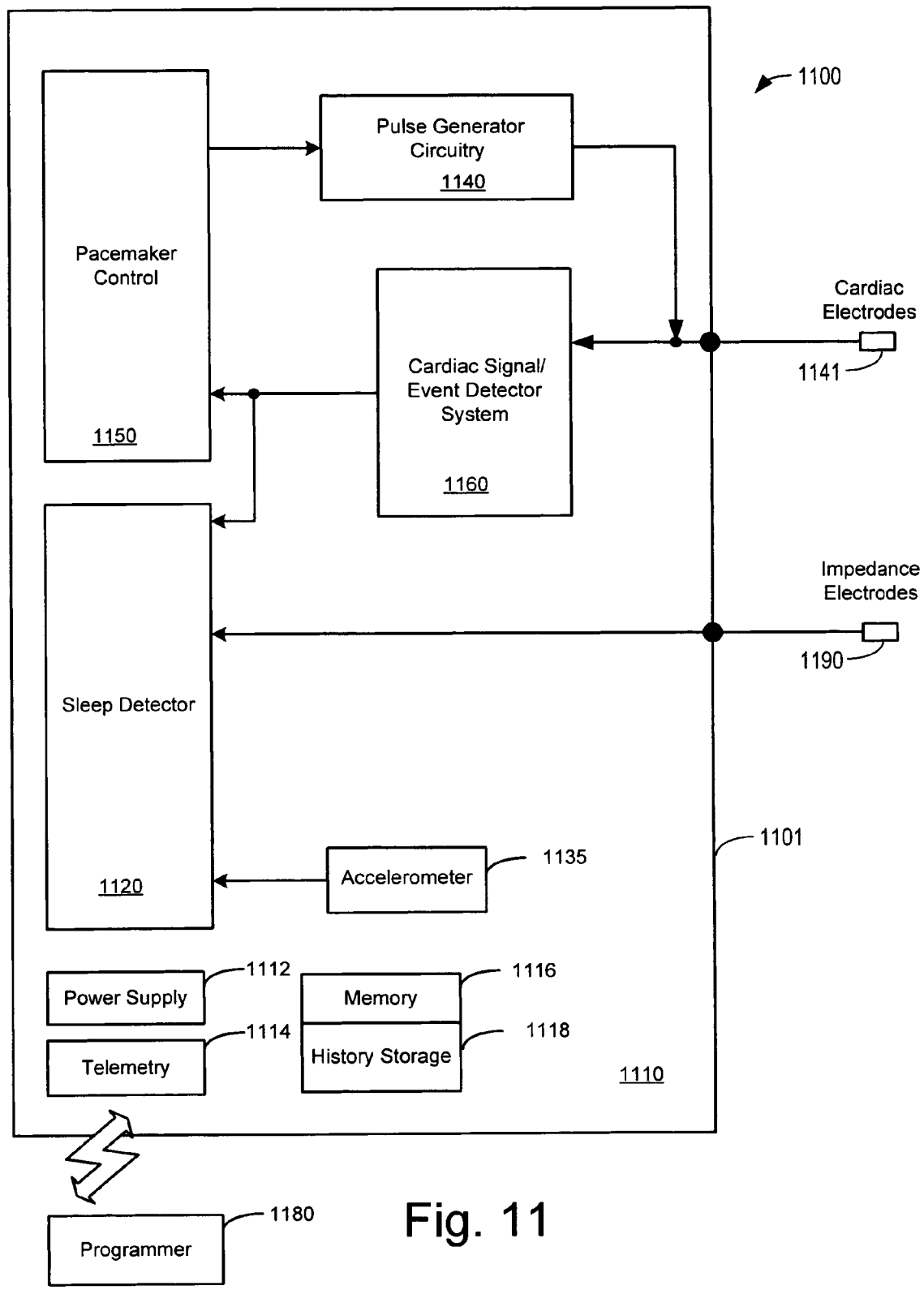
FIG. 11 is a block diagram of a cardiac rhythm management (CRM) system configured as a pacemaker and suitable for implementing a sleep detection methodology useful for coordinated diagnosis and/or therapy using gas analysis in accordance with embodiments of the invention.

Referring now to FIG. 11, there is shown a block diagram of an embodiment of a CRM system 1100 configured as a pacemaker and suitable for implantably detecting arousal and determining the presence of sleep disordered breathing in accordance with the invention. FIG. 11 shows the CRM 1100 divided into functional blocks. The CRM 1100 includes a sleep detector 1120 for receiving sleep-related signals and detecting sleep in accordance with embodiments of the invention.

In one embodiment, the sleep detector 1120 is incorporated as part of CRM circuitry 1110 encased and hermetically sealed in a housing 1101 suitable for implanting in a human body. Power to the CRM 1100 is supplied by an electrochemical battery power supply 1112 housed within the CRM 1100. A connector block (not shown) is additionally attached to the CRM 1100 to allow for the physical and electrical attachment of the cardiac lead system conductors to the CRM circuitry 1110.

The CRM circuitry 1110 may be configured as a programmable microprocessor-based system, with circuitry for detecting sleep in addition to providing pacing therapy to the heart. Cardiac signals sensed by one or more cardiac electrodes 1141 may be processed by the cardiac event detection circuitry 1160. Pace pulses controlled by the pacemaker control 1150 and generated by the pulse generator 1140 are delivered to the heart to treat various arrhythmias of the heart.

The memory circuit 1116 may store parameters for various device operations involved in sleep detection and/or cardiac pacing and sensing. The memory circuit 1116 may also store data indicative of sleep-related signals received by components of the CRM circuitry 1110, such as information derived from one or more impedance electrodes 1190, the cardiac signal detector system 1160, the accelerometer 1135, and/or the sleep detector 1120.

As illustrated in FIG. 11, the sleep detector 1120 receives signals derived from the cardiac event detector 1160, the impedance electrodes 1190 and the accelerometer 1135 to perform operations involving detecting sleep onset and sleep termination according to the principles of the invention. Historical data storage 1118 may be coupled to the sleep detection circuitry 1120 for storing historical sleep related data. Such data may be transmitted to an external programmer unit 1180 and used for various diagnostic purposes and as needed or desired.

Telemetry circuitry 1114 is coupled to the CRM circuitry 1110 to allow the CRM 1100 to communicate with a remote device such as the programmer 1180, or other device. In one embodiment, the telemetry circuitry 1114 and the programmer 1180 use a wire loop antenna and a radio frequency telemetric link to receive and transmit signals and data between the programmer 1180 and telemetry circuitry 1114. In this manner, programming commands and data may be transferred between the CRM circuitry 1110 and the one or more remote devices 1180 during and after implant.

The programming commands allow a physician to set or modify various parameters used by the CRM system 1100. These parameters may include setting sleep detection parameters for use during sleep detection, such as which sleep-related signals are to be used for sleep detection and threshold adjustment, and the initial sleep detection thresholds. In addition, the CRM system 1100 may download to the programmer 1180 stored data pertaining to sensed sleep periods, including the amount of time spent sleeping, the time of day sleep periods occurred, historical data of sleep times, and the number of arousals during the sleep periods, for example.

Still referring to FIG. 11, signals associated with patient activity may be detected through the use of an accelerometer 1135 positioned within the housing 1101 of the CRM 1100. The accelerometer 1135 may be responsive to patient activity. The accelerometer signal may be correlated with activity level or workload, for example. Signals derived from the accelerometer 1135 are coupled to the sleep detector 1120 and may also be used by the pacemaker 1150 for implementing a rate adaptive pacing regimen, for example.

The impedance electrodes 1190 sense the patient's transthoracic impedance. The transthoracic impedance may be used to calculate various parameters associated with respiration. Impedance driver circuitry (not shown) induces a current that flows through the blood between the impedance drive electrode and a can electrode on the housing 1101 of the CRM 1100. The voltage at an impedance sense electrode relative to the can electrode changes as the transthoracic impedance changes. The voltage signal developed between the impedance sense electrode and the can electrode is detected by the impedance sense amplifier and is delivered to the sleep detector circuitry 1120 for further processing.

Figure 12:
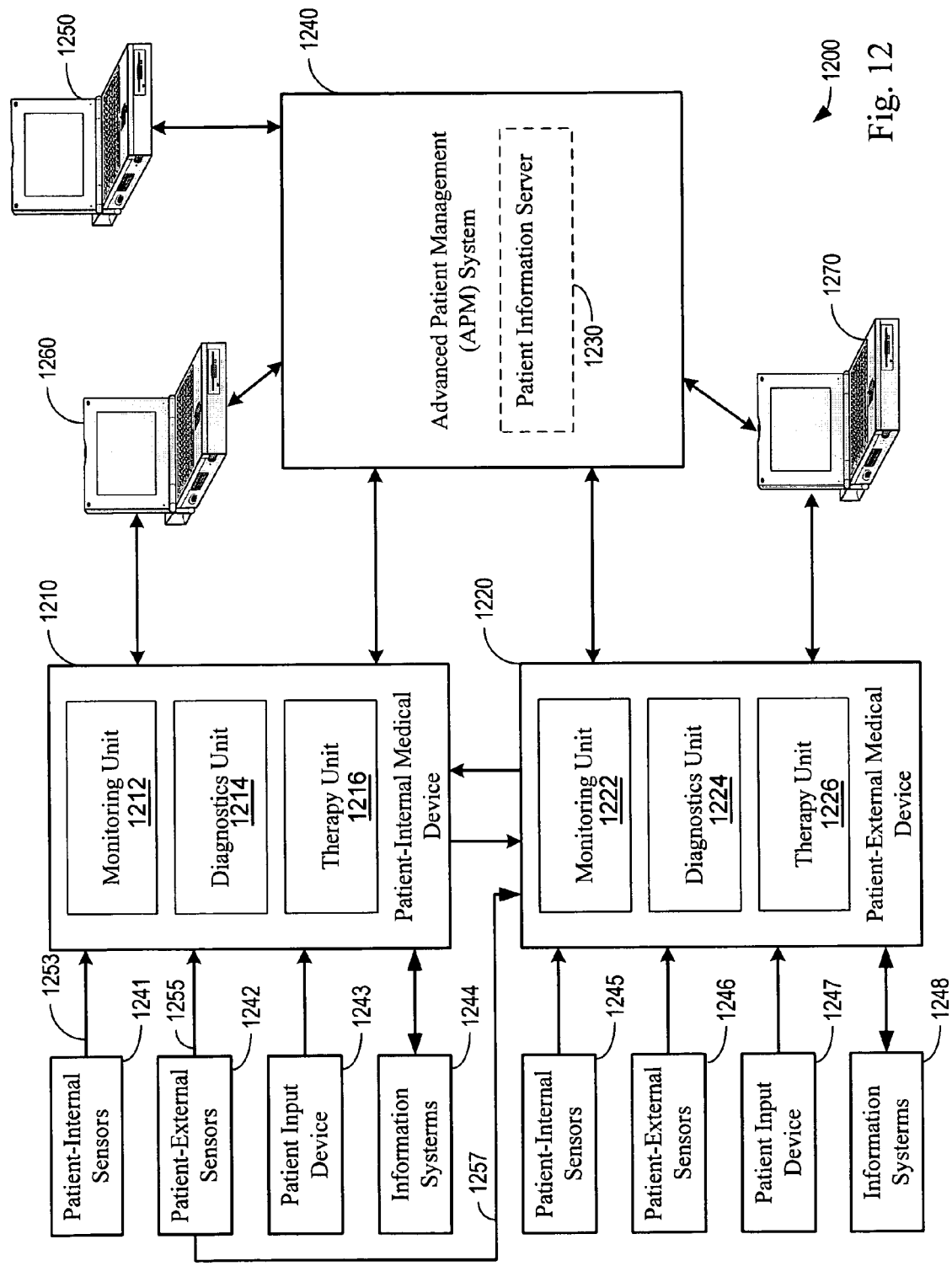
FIG. 12 is a block diagram of a medical system that may be used to implement coordinated patient monitoring, diagnosis, and/or therapy in accordance with embodiments of the invention.

FIG. 12 is a block diagram of a medical system 1200 that may be used to implement coordinated patient measuring and/or monitoring, diagnosis, and/or therapy, including detecting arousal and determining the presence of sleep disordered breathing, a pulmonary disorder, and/or a cardiac disorder in accordance with embodiments of the invention. The medical system 1200 may include, for example, one or more patient-internal medical devices 1210 and one or more patient-external medical devices 1220. Each of the patient-internal 1210 and patient-external 1220 medical devices may include one or more of a patient monitoring unit 1212, 1222, a diagnostics unit 1214, 1224, and/or a therapy unit 1216, 1226.

The patient-internal medical device 1210 is typically a fully or partially implantable device that performs measuring, monitoring, diagnosis, and/or therapy functions. The patient-external medical device 1220 performs monitoring, diagnosis, and/or therapy functions external to the patient (i.e., not invasively implanted within the patient's body). The patient-external medical device 1220 may be positioned on the patient, near the patient, or in any location external to the patient. It is understood that a portion of a patient-external medical device 1220 may be positioned within an orifice of the body, such as the nasal cavity or mouth, yet may be considered external to the patient (e.g., mouth pieces/appliances, tubes/appliances for nostrils, or temperature sensors positioned in the ear canal).

The patient-internal and patient-external medical devices 1210, 1220 may be coupled to one or more sensors 1241, 1242, 1245, 1246, patient input devices 1243, 1247, and/or other information acquisition devices 1244, 1248. The sensors 1241, 1242, 1245, 1246, patient input devices 1243, 1247, and/or other information acquisition devices 1244, 1248 may be employed to detect conditions relevant to the monitoring, diagnostic, and/or therapeutic functions of the patient-internal and patient-external medical devices 1210, 1220.

The medical devices 1210, 1220 may each be coupled to one or more patient-internal sensors 1241, 1245 that are fully or partially implantable within the patient. The medical devices 1210, 1220 may also be coupled to patient-external sensors positioned on, near, or in a remote location with respect to the patient. The patient-internal and patient-external sensors are used to sense conditions, such as physiological or environmental conditions, that affect the patient.

The patient-internal sensors 1241 may be coupled to the patient-internal medical device 1210 through one or more internal leads 1253. In one example, as was described above with reference to FIG. 9, an internal endocardial lead system is used to couple cardiac electrodes to an implantable pacemaker or other cardiac rhythm management device. Still referring to FIG. 12, one or more patient-internal sensors 1241 may be equipped with transceiver circuitry to support wireless communications between the one or more patient-internal sensors 1241 and the patient-internal medical device 1210 and/or the patient-external medical device 1220. The patient-external sensors 1242 may be coupled to the patient-internal medical device 1210 and/or the patient-external medical device 1220 through one or more internal leads 1255 or through wireless connections. Patient-external sensors 1242 may communicate with the patient-internal medical device 1210 wirelessly. Patient-external sensors 1246 may be coupled to the patient-external medical device 1220 through one or more internal leads 1257 or through a wireless link.

The medical devices 1210, 1220 may be coupled to one or more patient input devices 1243, 1247. The patient input devices are used to allow the patient to manually transfer information to the medical devices 1210, 1220. The patient input devices 1243, 1247 may be particularly useful for inputting information concerning patient perceptions, such as how well the patient feels, and information such as patient smoking, drug use, or other activities that are not automatically sensed or detected by the medical devices 1210, 1220.

The medical devices 1210, 1220 may be connected to one or more information acquisition devices 1244, 1248, for example, a database that stores information useful in connection with the monitoring, diagnostic, or therapy functions of the medical devices 1210, 1220. For example, one or more of the medical devices 1210, 1220 may be coupled through a network to a patient information server 1230 that provides information about environmental conditions affecting the patient, e.g., the pollution index for the patient's location.

In one embodiment, the patient-internal medical device 1210 and the patient-external medical device 1220 may communicate through a wireless link between the medical devices 1210, 1220. For example, the patient-internal and patient-external devices 1210, 1220 may be coupled through a short-range radio link, such as Bluetooth, IEEE 802.11, and/or a proprietary wireless protocol. The communications link may facilitate uni-directional or bidirectional communication between the patient-internal 1210 and patient-external 1220 medical devices. Data and/or control signals may be transmitted between the patient-internal 1210 and patient-external 1220 medical devices to coordinate the functions of the medical devices 1210, 1220.

In another embodiment, the patient-internal and patient-external medical devices 1210, 1220 may be used within the structure of an advanced patient management system 1240. Advanced patient management systems 1240 involve a system of medical devices that are accessible through various communications technologies. For example, patient data may be downloaded from one or more of the medical devices periodically or on command, and stored at the patient information server 1230. The physician and/or the patient may communicate with the medical devices and the patient information server 1230, for example, to acquire patient data or to initiate, terminate or modify therapy.

The data stored on the patient information server 1230 may be accessible by the patient and the patient's physician through one or more terminals 1250, e.g., remote computers located in the patient's home or the physician's office. The patient information server 1230 may be used to communicate to one or more of the patient-internal and patient-external medical devices 1210, 1220 to provide remote control of the monitoring, diagnosis, and/or therapy functions of the medical devices 1210, 1220.

In one embodiment, the patient's physician may access patient data transmitted from the medical devices 1210, 1220 to the patient information server 1230. After evaluation of the patient data, the patient's physician may communicate with one or more of the patient-internal or patient-external devices 1210, 1220 through the APM system 1240 to initiate, terminate, or modify the monitoring, diagnostic, and/or therapy functions of the patient-internal and/or patient-external medical systems 1210, 1220. Systems and methods involving advanced patient management techniques are further described in U.S. Pat. Nos. 6,336,903, 6,312,378, 6,270,457, and 6,398,728, hereby incorporated herein by reference.

In another embodiment, the patient-internal and patient-external medical devices 1210, 1220 may not communicate directly, but may communicate indirectly through the APM system 1240. In this embodiment, the APM system 1240 may operate as an intermediary between two or more of the medical devices 1210, 1220. For example, data and/or control information may be transferred from one of the medical devices 1210, 1220 to the APM system 1240. The APM system 1240 may transfer the data and/or control information to another of the medical devices 1210, 1220.

In one embodiment, the APM system 1240 may communicate directly with the patient-internal and/or patient-external medical devices 1210, 1220. In another embodiment, the APM system 1240 may communicate with the patient-internal and/or patient-external medical devices 1210, 1220 through medical device programmers 1260, 1270 respectively associated with each medical device 1210, 1220.

Various embodiments described herein may be used in connection with advanced patient management. Methods, structures, and/or techniques described herein relating to advanced patient management, such as those involving remote patient/device monitoring, diagnosis, therapy, or other advanced patient management related methodologies, may incorporate features of one or more of the following references: U.S. Pat. Nos. 6,221,011; 6,277,072; 6,280,380; 6,358,203; 6,368,284; and 6,440,066 each hereby incorporated herein by reference.

A number of the examples presented herein involve block diagrams illustrating functional blocks used for coordinated monitoring, diagnosis, and/or therapy functions in accordance with embodiments of the invention. It will be understood by those skilled in the art that there exist many possible configurations in which these functional blocks may be arranged and implemented. The examples depicted herein provide examples of possible functional arrangements used to implement the approaches of the invention.

Each feature described in this specification (including any accompanying claims, abstract, and drawings) may be replaced or enhanced by alternative features having the same, equivalent or similar purpose, unless expressly stated otherwise. Thus, unless expressly stated otherwise, each feature described is one example only of a generic series of equivalent or similar features.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of providing disordered breathing therapy for a patient whose respiration cycle includes inspiration and expiration intervals, comprising:

providing a patient-external respiratory therapy and a patient-internal cardiac therapy to a patient, the respiratory therapy being adapted to treat disordered breathing;

measuring an expired respiratory gas concentration of an expired respiratory gas sample acquired at the end of an expiration interval of the patient as determined by a timing element, the measured expired respiratory gas concentration representative of blood gas concentration;

determining one or more parameters influenced by disordered breathing, the one or more parameters comprising at least the expired respiratory gas concentration;

providing one or more parameter thresholds comprising at least an expired respiratory gas threshold; and adjusting the respiratory therapy and the cardiac therapy based on the one or more parameters and the one or more parameter thresholds.

2. The method of claim 1, the one or more parameters further comprising blood pH measured by a sensor.

3. The method of claim 1, wherein determining the one or more parameters comprises determining the one or more parameters using one or more implantable sensors.

4. The method of claim 1, wherein determining the one or more parameters comprises determining the one or more parameters using one or more patient-external sensors.

5. The method of claim 1, wherein determining the one or more parameters comprises determining the one or more parameters using one or more implantable sensors and one or more patient-external sensors.

6. The method of claim 1, wherein adjusting the respiratory therapy comprises adjusting a positive airway pressure therapy.

7. The method of claim 1, wherein adjusting the cardiac therapy comprises adjusting a cardiac pacing therapy.

8. The method of claim 1, wherein determining the one or more parameters comprises determining one or both of expired oxygen concentration or carbon dioxide gas concentration.

9. The method of claim 1, wherein determining the one or more parameters comprises determining one or more of blood oxygen concentration, blood carbon dioxide concentration, or blood pH.

10. The method of claim 1, further comprising monitoring for a change in the one or more parameters.

11. The method of claim 10, wherein monitoring for the change in the one or more parameters comprises detecting a change in the one or more parameters indicative of hypoxemia.

12. The method of claim 10, wherein monitoring for the change in the one or more parameters comprises detecting a change in the one or more parameters indicative of apnea.

13. The method of claim 10, wherein monitoring for the change in the one or more parameters comprises detecting a change in the one or more parameters indicative of hypercapnea or hypocapnea.

14. The method of claim 1, wherein adjusting the respiratory therapy and the cardiac therapy comprises using the therapy controller of a patient-external system for adjusting one or both of the respiratory therapy and the cardiac therapy.

15. A method of providing disordered breathing therapy for a patient whose respiration cycle includes inspiration and expiration, comprising:

providing a patient-external respiratory therapy and a patient-internal cardiac therapy to a patient, the respiratory therapy being adapted to treat disordered breathing;

measuring an expired respiratory gas concentration of an expired respiratory gas sample acquired at the end of an expiration interval of the patient as determined by a timing element, the measured expired respiratory gas concentration representative of blood gas concentration;

determining one or more parameters influenced by disordered breathing, the one or more parameters comprising at least the expired respiratory gas concentration;

providing one or more parameter thresholds comprising at least an expired respiratory gas threshold; and adjusting, using a therapy controller, the respiratory therapy and the cardiac therapy based on the one or more parameters and the one or more parameter thresholds.

16. The method of claim 15, wherein the one or more parameters further comprise blood gas concentration or blood pH.

17. The method of claim 15, wherein determining the one or more parameters comprises determining the one or more parameters using one or more implantable sensors.

18. The method of claim 15, wherein adjusting the respiratory therapy comprises adjusting a positive airway pressure therapy.

19. The method of claim 15, wherein adjusting the cardiac therapy comprises adjusting a cardiac pacing therapy.

20. The method of claim 15, wherein adjusting the respiratory therapy and the cardiac therapy comprises using the therapy controller of a patient-external system for adjusting one or both of the respiratory therapy and the cardiac therapy.

21. The method of claim 15, wherein determining the one or more parameters comprises determining one or more of expired oxygen concentration, carbon dioxide gas concentration, blood oxygen concentration, blood carbon dioxide concentration, and blood pH.

22. The method of claim 15, further comprising monitoring the one or more parameters and detecting a change in the one or more parameters indicative of at least one of hypoxemia, apnea, hypercapnea or hypocapnea.

23. A method of providing disordered breathing therapy for a patient whose breathing includes inspiration and expiration, comprising:

providing a patient-external respiratory therapy and a patient-internal cardiac therapy to a patient, the respiratory therapy being adapted to treat disordered breathing;

measuring an expired respiratory gas concentration of an expired respiratory gas sample acquired at the very end of the patient's expiration just before inhalation starts as determined by a timing element, the measured expired respiratory gas concentration representative of blood gas concentration;

determining one or more parameters influenced by disordered breathing, the one or more parameters comprising at least the expired respiratory gas concentration;

providing one or more parameter thresholds comprising at least an expired respiratory gas threshold; and adjusting, using a therapy controller disposed in an implantable housing, the respiratory therapy and the cardiac therapy based on the one or more parameters and the one or more parameter thresholds.

24. The method of claim 23, wherein the one or more parameters further comprise blood gas concentration or blood pH.

25. The method of claim 23, wherein determining the one or more parameters comprises determining the one or more parameters using one or more implantable sensors.

26. The method of claim 23, wherein adjusting the respiratory therapy comprises adjusting a positive airway pressure therapy.

27. The method of claim 23, wherein adjusting the cardiac therapy comprises adjusting a cardiac pacing therapy.

28. The method of claim 23, wherein adjusting the respiratory therapy and the cardiac therapy comprises using the therapy controller of a patient-external system for adjusting one or both of the respiratory therapy and the cardiac therapy.

29. The method of claim 23, wherein determining the one or more parameters comprises determining one or more of expired oxygen concentration, carbon dioxide gas concentration, blood oxygen concentration, blood carbon dioxide concentration, and blood pH.

30. The method of claim 23, further comprising monitoring the one or more parameters and detecting a change in the one or more parameters indicative of at least one of hypoxemia, apnea, hypercapnea or hypocapnea.

* * * * *